(12) United States Patent
Scherch et al.

(10) Patent No.: US 7,590,218 B2
(45) Date of Patent: Sep. 15, 2009

(54) SYSTEM FOR MONITORING THE GEOMETRY OF A RADIATION TREATMENT APPARATUS, TRACKABLE ASSEMBLY, PROGRAM PRODUCT, AND RELATED METHODS

(75) Inventors: John David Scherch, Pittsburgh, PA (US); Edward Charles Smetak, Katy, TX (US)

(73) Assignee: Best Medical International, Inc., Springfield, VA (US)

( * ) Notice: Subject to any disclaimer, the term of this patent is extended or adjusted under 35 U.S.C. 154(b) by 108 days.

(21) Appl. No.: 11/374,572

(22) Filed: Mar. 14, 2006

(65) Prior Publication Data

US 2006/0215813 A1 Sep. 28, 2006

Related U.S. Application Data

(60) Provisional application No. 60/664,513, filed on Mar. 23, 2005.

(51) Int. Cl.
*A61N 5/10* (2006.01)
(52) U.S. Cl. .......................................... 378/65; 378/205
(58) Field of Classification Search .................. 378/65, 378/205–206, 208, 37, 207; 600/427, 426, 600/414
See application file for complete search history.

(56) References Cited

U.S. PATENT DOCUMENTS

| | | | |
|---|---|---|---|
| 3,861,807 | A | 1/1975 | Lescrenier et al. |
| 3,987,281 | A | 10/1976 | Hodes et al. |
| 4,396,945 | A | 8/1983 | DiMatteo et al. |
| 4,455,609 | A | 6/1984 | Inamura et al. |
| 4,649,504 | A | 3/1987 | Krouglicof et al. |
| 5,197,476 | A | 3/1993 | Nowacki et al. |
| 5,227,985 | A | 7/1993 | DeMenthon |

(Continued)

FOREIGN PATENT DOCUMENTS

DE 103 35 037 A1 3/2005

(Continued)

OTHER PUBLICATIONS

This application is related to U.S. Appl. No. 11/005,643, titled "System for Analyzing the Geometry of a Radiation Treatment Apparatus, Software, and Related Methods," filed on Dec. 6, 2004 (not published).

*Primary Examiner*—Hoon Song
(74) *Attorney, Agent, or Firm*—Bracewell & Giuliani LLP

(57) ABSTRACT

A system to monitor a geometry of a treatment apparatus, an apparatus, a trackable assembly, program product, and methods are provided. The system includes a treatment apparatus having a radiation emitter, a rotating assembly controlled by a controller, and an application computer, which provides treatment delivery instructions to the controller. The system can also include a trackable assembly connected to the rotating assembly and having a fixedly connected first trackable body which functions as a reference fixture and a pivotally connected second trackable body which provides data used to determine a rotation angle of the rotating assembly. The system also includes an apparatus to track a trackable body which has a trackable body detector to detect a position of the indicators carried by the first and the second trackable bodies and a determiner to determine and verify the location of the origin of an isocenter coordinate system and to determine rotational path data about the rotating assembly.

47 Claims, 11 Drawing Sheets

U.S. PATENT DOCUMENTS

| | | | |
|---|---|---|---|
| 5,373,844 A | 12/1994 | Smith et al. | |
| 5,411,026 A | 5/1995 | Carol | |
| 5,511,549 A | 4/1996 | Legg et al. | |
| 5,596,619 A | 1/1997 | Carol | |
| 5,622,187 A | 4/1997 | Carol | |
| 5,754,623 A | 5/1998 | Seki et al. | |
| 5,772,594 A | 6/1998 | Barrick | |
| 5,802,136 A | 9/1998 | Carol | |
| 5,828,770 A | 10/1998 | Leis et al. | |
| 6,032,066 A | 2/2000 | Lu et al. | |
| 6,038,283 A | 3/2000 | Carol et al. | |
| 6,285,902 B1 * | 9/2001 | Kienzle et al. | 600/427 |
| 6,288,785 B1 | 9/2001 | Frantz et al. | |
| 6,325,758 B1 | 12/2001 | Carol et al. | |
| 6,360,116 B1 | 3/2002 | Jackson et al. | |
| 6,393,096 B1 | 5/2002 | Carol et al. | |
| 6,405,072 B1 | 6/2002 | Cosman | |
| 6,435,717 B1 | 8/2002 | Koehler et al. | |
| 6,535,574 B1 * | 3/2003 | Collins et al. | 378/65 |
| 6,560,311 B1 | 5/2003 | Shepard et al. | |
| 2002/0080915 A1 | 6/2002 | Frohlich et al. | |
| 2002/0122530 A1 | 9/2002 | Erbel et al. | |
| 2002/0188194 A1 * | 12/2002 | Cosman | 600/426 |
| 2002/0193685 A1 | 12/2002 | Mate et al. | |
| 2004/0015077 A1 | 1/2004 | Sati et al. | |
| 2004/0122311 A1 | 6/2004 | Cosman | |
| 2004/0138556 A1 | 7/2004 | Cosman | |
| 2005/0020917 A1 | 1/2005 | Scherch | |
| 2005/0215888 A1 * | 9/2005 | Grimm et al. | 600/426 |

FOREIGN PATENT DOCUMENTS

| | | |
|---|---|---|
| EP | 0 910 990 A1 | 4/1999 |
| EP | 0911065 A | 4/1999 |
| EP | 1041918 | 11/2000 |
| EP | 1 419 801 A | 5/2004 |
| WO | WO 99/27839 A2 | 6/1999 |
| WO | WO 00/47103 A2 | 8/2000 |
| WO | WO 00/56215 A1 | 9/2000 |
| WO | WO 01/06924 A1 | 2/2001 |
| WO | WO 02/09588 A | 2/2002 |
| WO | WO 02/49044 A2 | 6/2002 |
| WO | WO 2005/018734 A | 3/2005 |
| WO | WO 2005/099819 A | 10/2005 |

* cited by examiner

SYSTEM FOR MONITORING THE GEOMETRY OF A RADIATION TREATMENT APPARATUS, TRACKABLE ASSEMBLY, PROGRAM PRODUCT, AND RELATED METHODS

RELATED APPLICATIONS

This application is related to and claims priority to and the benefit of U.S. Provisional Application No. 60/664,513, filed on Mar. 23, 2005, incorporated herein by reference in its entirety.

BACKGROUND OF THE INVENTION

1. Field of the Invention

The present invention relates to patient therapy. More specifically, the present invention relates to a system, a trackable assembly, program product, and related methods for monitoring a geometry of a radiation treatment apparatus to verify the origin and directions of a coordinates system used during treatment plan delivery.

2. Description of the Related Art

Radiation therapy can be effective in treating certain types of cancerous tumors, lesions, or other "targets." A vast majority of such targets can be eradicated completely if a sufficient radiation dose is delivered to the tumor or lesion volume. Complications, however, may result from use of the necessary effective radiation dose, due to damage to healthy tissue which surrounds the target, or to other healthy body organs located close to the target. The goal of various radiation procedures, such as conformal radiation therapy treatment, is to confine the delivered radiation dose to only the target volume defined by the outer surfaces of the target, while minimizing the dose of radiation to surrounding healthy tissue or adjacent healthy organs. If the effective radiation dose is not delivered to the proper location within the patient, serious complications may result.

Radiation therapy treatment typically uses a radiation delivery apparatus or device, such as a linear accelerator or other radiation producing source, to treat the target. For example, the conventional linear accelerator includes a rotating gantry which generally rotates about a horizontal axis and which has a radiation beam source positionable about the patient which can direct a radiation beam toward the target to be treated. The linear accelerator can also include a rotating treatment table which generally rotates about a vertical axis and which can position the target within a rotational plane of the rotating gantry. Various types of apparatus can further conform the shape of the radiation treatment beam to follow the spatial contour of the target as seen by the radiation treatment beam, from a linear accelerator, as it passes through the patient's body into the target during rotation of the radiation beam source. Multileaf collimators having multiple leaf or finger projections can be programmed to move individually into and out of the path of the radiation beam to shape the radiation beam.

Various types of radiation treatment planning systems can create a radiation treatment plan, which, when implemented, will deliver a specified dose of radiation shaped to conform to the target volume, while limiting the radiation dose delivered to sensitive surrounding healthy tissue or adjacent healthy organs or structures. Typically, the patient has the radiation therapy treatment plan prepared, based upon a diagnostic study through the use of computerized tomographic ("CT") scanning, magnetic resonance ("MR") imaging, or conventional simulation films, which are plain x-rays generated with the patient, and thus, the patient's tumor or lesion in the position which will be used during the radiation therapy treatment.

Regardless of which radiation generating apparatus or technique is used at the time of the diagnostic study to develop the radiation therapy treatment plan, in the delivery of either conformal radiation therapy treatments or static radiation therapy treatments, etc., the position of the target with respect to the radiation delivery apparatus is very important. Successful radiation therapy depends on accurately placing the radiation beam in the proper position upon the target. Thus, it is necessary to relate the position of the target at the time of the diagnostic study to how the target will be positioned at the time of the radiation therapy treatment. It is also necessary to maintain an alignment between the radiation delivery apparatus and the target throughout the delivery of the radiation therapy. If this positional relationship is not correct, the radiation dose may not be delivered to the correct location within the patient's body, possibly under treating the target tumor or lesion and damaging healthy surrounding tissue and organs.

Placement of the radiation beams in the proper juxtaposition with the patient to be treated can be accomplished by referencing both the radiation beam and the patient position to a coordinate system referred to as the isocenter coordinate system, which is defined by the geometry of the radiation delivery apparatus. In the linear accelerator example, the gantry, the treatment table, and collimator each have axes of rotation designed to intersect at a specific location in the middle of a treatment room, referred to as the isocenter, an origin of an interesting coordinate system of the treatment room, correspondingly referred to as the isocenter coordinate system. The isocenter coordinate system is nominally defined as horizontal (x-axis), vertical (z-axis), and co-linear with the axis of gantry rotation (y-axis). The isocenter of these three axis of interest is determined and used as a reference "point" to orient the target to the radiation treatment plan during treatment plan development and subsequent radiation delivery.

In order to deliver the radiation therapy in accordance with the radiation plan, the position of the patient is adjusted to dispose the target at the isocenter of the linear accelerator. In general, the patient is positioned on the treatment table of the radiation delivery apparatus to conform to the position used during formulation of the treatment plan. The treatment table is further rotated to then dispose the target at the isocenter to align the view of the target with that view expected by the collimator or other radiation delivery apparatus of the linear accelerator, according to the radiation treatment plan. The treatment table is then locked in place, and the patient is immobilized so that the radiation therapy treatment can be started.

Also, in the linear accelerator example, the isocenter of gantry rotation is the point where the radiation beams from the collimator intersect as the gantry of the linear accelerator carrying the radiation beam source rotates around the target in the patient. There are various methodologies of determining the location of this isocenter. For example, one methodology of determining the isocenter of gantry rotation includes attaching to the gantry a marking device, such as a long rod holding a marking implement, positioning a vertically oriented sheet of receiving material, such as paper, adjacent the marking device. The gantry is then rotated to form an arc or a circle on the receiving material. The operator can then examine the arc or circle to determine the origin of the circle, which relates to the isocenter. Also for example, the operator can actually deploy the radiation beam in order to measure the direction of the radiation beam during rotation of the gantry.

Other physical measurements can also be taken to help the operator determine an approximate location of the isocenter. For example, described in co-pending application Ser. No. 11/005,643, by Scherch et al., entitled "System for Analyzing the Geometry of a Radiation Treatment Apparatus, Software and Related Methods," incorporated by reference, is a system, apparatus, software and methods that can measure the rotation of various components of the mechanical system of the radiation treatment apparatus or device to determine the location of the radiation beam and the positioning of the patient in order to precisely define the isocenter coordinate system used by the operator.

Regardless of the methodology used to determine isocenter, once the isocenter coordinate system has been determined, the radiation beam arrangement and patient positioning can be referenced to the isocenter. Lasers, typically mounted on the wall of the treatment room, are then pointed or directed to cross at the isocenter to identify the location of the isocenter.

Recognized by the Applicants, however, is that the above described methodologies of determining isocenter generally do not account for continuing degradation of the gantry during the actual delivery of the radiation treatment. Also, existing systems, which indicate to the operator the position of the isocenter coordinate system, i.e., the above described lasers, are not accessible during the course of the radiation treatment. Therefore, many systems must rely on the accuracy of a calibrated tracking system to reliably indicate the isocenter coordinate system during radiation delivery. Also recognized, however, is that these systems are vulnerable to inadvertent changes in that calibrated position.

Specifically, the "camera" of the optical tracking system is typically structurally removed from the gantry by a great distance and fixedly connected to a wall or ceiling mount. This "rigid mounting" of the camera may actually move around relative to isocenter. Even slight movements in the camera mounting can have a significant effect on the accuracy of the optical tracking system, due to the great distance between itself and the isocenter, and thus, the optical tracking system requires a specific pre-operation "morning" quality assurance examination to determine if any such changes have occurred.

Thus, also recognized by the Applicants is the need for a system, an assembly, program product, and related methods for continuously monitoring a geometry of a treatment apparatus or device during treatment to continuously verify the origin and orientation of a coordinate system used by the tracking system or device to reference the radiation beam and the patient position to accurately place a radiation beam in a proper juxtaposition with the patient being treated.

SUMMARY OF THE INVENTION

In view of the foregoing, embodiments of the present invention advantageously provide a system, trackable assembly, program product, and methods related to monitoring a geometry of an apparatus of having at least one rotating assembly. Embodiments of the present invention advantageously provide a system, trackable assembly, program product, and methods related to monitoring a geometry of a radiation treatment or generating apparatus to verify the origin and directions of a coordinates system used during patient treatment delivery to reference radiation beam and patient positioning. Advantageously, embodiments of the present invention include a system, trackable assembly, program product, and methods that can also monitor the rotation of various rotating assemblies of a mechanical system of the treatment apparatus during radiation delivery to continuously verify the origin (isocenter) and orientation of the isocenter coordinate system used to reference radiation beam and patient positioning. This information can be used to calibrate the treatment plan to the isocenter coordinate system used by the operator so that a treatment plan can be more accurately applied. Advantageously, embodiments of the present invention also provide a system including a trackable assembly, program product, and methods that can measure three-dimensional points in space at locations along the maximum rotational arc or path of a rotating assembly of the treatment apparatus, such as, a rotating gantry assembly. These measurements can be used to adapt the planned radiation treatment to improve its accuracy and efficiency. Advantageously, analyzed and indicated can be imperfections in the mechanical system of the radiation treatment apparatus which might normally be ignored or misinterpreted during radiation delivery.

Generally, embodiments of the present invention provide a system that includes a treatment apparatus, typically in the form of a linear accelerator, having a radiation emitter, at least one rotating assembly controlled by a controller, and an application computer which provides treatment delivery instructions to the controller. The system also includes a trackable assembly connected to a rotating assembly. The trackable assembly includes a fixedly connected first trackable body, having a plurality of indicators positioned thereon, which functions as a reference fixture, and can include a pivotally connected second trackable body, also having a plurality of indicators positioned thereon, which provides data used to determine rotation angle of the rotating assembly. The system also includes an apparatus to track a trackable body hereinafter referred to as a "trackable body tracking apparatus," which includes a trackable body detector provided to detect a position of the indicators, and a determiner in communication with the trackable body detector to determine the position and orientation of the first and the second trackable bodies, to thereby determine the location and orientation of the origin of a coordinate system, used by a therapist, and referred to as the isocenter of an isocenter coordinate system, and to thereby determine rotational path data about the rotating assembly.

More specifically, in an embodiment of the present invention, the system includes an apparatus, preferably in the form of a radiation treatment apparatus which delivers radiation to a target in a patient. An application computer having a memory associated therewith and a treatment plan stored in the memory provides treatment delivery instructions to the treatment apparatus. The treatment apparatus has the radiation emitter positioned to emit a radiation beam having a beam axis, a controller to control delivery of the radiation beam to the patient, and a rotating assembly having a rotational path in a distinct plane and an axis of rotation functioning to direct the radiation beam through a target of a patient in accordance with signals from the controller. The axis of rotation of the rotating assembly generally intersects with the beam axis at a three-dimensional coordinate, which defines the isocenter or origin of the isocenter coordinate system of the treatment apparatus.

The system includes a trackable body tracking apparatus including a preferably optical trackable body detector or camera subsystem and a determiner. The trackable body detector includes a detector body positioned spaced apart from the treatment apparatus and a trackable assembly. A trackable assembly is positioned to be viewed/detected by the trackable body detector. The trackable assembly includes a first trackable body fixedly connected to a preselected portion of the rotating assembly at a predetermined offset position relative to a predetermined three-dimensional coordinate system definition of the three-dimensional coordinate position of the isocenter and along the rotational path of the rotating assembly. The first trackable body has a plurality of separate and spaced-apart indicators each connected at a separate preselected position thereon to indicate to the trackable body detector separate three-dimensional coordinate positions of each indicator of the plurality of indicators. Correspondingly, the trackable body detector has a receiver positioned to receive energy to thereby detect three-dimensional positions and to produce a plurality of position signals indicating three-dimensional coordinate positions of the trackable assembly indicators. The indicators are preferably in the form of passive indicators such as, for example, retro-reflective spheres which advantageously provide upwards of a 180 degree reflective field of view and decrease inherent wiring requirements associated with active indicators. In such configuration, the trackable body detector also includes an emitter to energize the indicators.

The determiner, in communication with the trackable body detector and responsive to the plurality of position signals produced by the detector, can determine (in trackable body detector/camera space) the three-dimensional coordinate position of the isocenter and/or orientation of the isocenter coordinate system with reference to the first trackable body through use of a predetermined transform matrix stored in the memory of the determiner can provide or indicate a transform (magnitude, direction, and rotation) between a predetermined or preselected trackable body reference coordinate system (i.e. position and orientation) of first trackable body and a predetermined isocenter coordinate system (i.e. physical three-dimensional coordinate position of the isocenter and orientation of the isocenter coordinate system). The trackable body detector can detect the first trackable body and the determiner can determine a separate transform matrix between the trackable body detector coordinate system and the first trackable body coordinate system. Having a chain of transformation matrices, the determiner can thus transform the three-dimensional coordinate system definition of the isocenter to detector/camera space. Note, the determination of the three-dimensional coordinate system definition of the isocenter in trackable body detector/camera space is generally referred to as calibrating the trackable body tracking apparatus to a location and orientation in space of the physical three-dimensional coordinate position of the isocenter.

In an embodiment of the present invention, the determiner can also detect or determine a possible isocenter coordinate system definition failure (described later), when so existing. In this embodiment, the trackable body detector is fixedly mounted or immobilized and can function as a reference fixture. The trackable body detector is assigned a trackable body tracking apparatus coordinate system having a fixed relationship with the trackable body detector defining a trackable body detector offset position. To detect or determine the possible isocenter coordinate system definition failure, the determiner can determine the three-dimensional coordinate system definition of the isocenter with reference to the trackable body detector, rather than the first trackable body, through use of a predetermined transform matrix stored in the memory of the determiner which provides or indicates a transform between a trackable body detector reference coordinate system and the predetermined isocenter coordinate system. The separately determined three-dimensional coordinate system definitions of the isocenter can then be compared, whereby a substantial difference indicates a possible isocenter coordinate system definition failure.

As an alternative methodology of detecting or determining a possible isocenter coordinate system definition failure, in an embodiment of the present invention, the determiner can determine a plurality of sampled three-dimensional coordinate first trackable body positions along the rotational path of the rotating assembly. The determined positions provide current rotational path data that can be compared to a predetermined rotational path of the rotating assembly stored in the memory of the determiner. A possible isocenter coordinate system definition failure is indicated if either of the plurality of determined first trackable body positions substantially deviate from a position substantially coincident with the predetermined rotational path of the rotating assembly.

The first trackable body, being connected to a rotating assembly, by its nature, can generally only be used to produce a reference to the isocenter coordinate system having coordinate system axes oriented relative to the orientation of the first trackable body, which, in the above described configuration, is variable. Thus, advantageously, in an embodiment of the present invention, the trackable assembly can also include a second trackable body which can be utilized to determine or to correct the relative orientation of the isocenter coordinate system determined with reference to the first trackable body. This is generally required when the rotating assembly is rotated off an initial reference position. To this end, the second trackable body has a proximal body end portion pivotally connected to or adjacent the first trackable (preferably flat) body, a free-moving distal body end portion, a medial body portion connected to and extending between the proximal body end portion and the distal body end portion. The medial body portion has a plurality of separate and spaced-apart indicators each connected at a separate preselected position of the second trackable body also to indicate to the trackable body detector a three-dimensional coordinate position of each indicator. The proximal and distal end configuration preferably provides a pendulum-type action which, responsive to gravity, allows the second trackable body to maintain a constant orientation which can be used by the determiner as a reference orientation. This reference orientation allows the determiner to correct the orientation of isocenter coordinate system determined with reference to the first trackable body resulting from a rotational error existing when the rotating assembly carrying the trackable assembly is rotated.

To determine the orientation of the isocenter coordinate system, the determiner first determines the orientations of the first and second trackable bodies, respectively. The determiner can then determine the rotation angle of the first trackable body, which relates to the rotational position of the rotating assembly from an initial reference position. This can be accomplished by determining an angular difference in orientation between the first and the second trackable trackable bodies. The correct orientation of the isocenter coordinate system can be determined by conceptually rotating the reference orientation of the isocenter coordinate system, determined from the first trackable body, by an amount related to the angular difference between the respective orientations of the first and the second trackable bodies. Thus, advantageously an accurate reference orientation (and position) of the isocenter coordinate system is provided using the same predetermined transform matrix regardless of the rotational orientation of the first trackable body, which can vary due to rotation of the rotating assembly for which the trackable assembly is connected.

The function of the determiner can be implemented in hardware and/or software/program product. In the preferred embodiment of the present invention, however, the function of the determiner is implemented almost entirely in software/program product either preloaded in memory of the determiner or contained on separate storage media. Correspondingly, the system can further include a program product, such as geometry analyzing program product, to analyze treatment apparatus geometry. The geometry analyzing program product includes a trackable body position determiner, that is adapted to receive and is responsive to the plurality of position signals produced by a trackable body detector which indicate a separate three-dimensional coordinate position of a plurality of separate and spaced-apart trackable indicators connected to a first trackable body. The trackable body position determiner determines a three-dimensional coordinate trackable body position of the first trackable body. An isocenter position determiner, determines a first three-dimensional coordinate position of the isocenter in response to the determined three-dimensional coordinate position of the first trackable body and a first predetermined transform matrix indicating a transform between a predetermined first trackable body reference coordinate system and a predetermined isocenter coordinate system of the treatment apparatus.

In an embodiment of the present invention having the previously described second trackable body, the orientation of the isocenter coordinate system can also be determined. A trackable body orientation determiner, responsive to the plurality of position signals produced by the trackable body detector, can determine a first trackable body orientation of the first trackable body and a second trackable body orientation of the second trackable body. An isocenter orientation determiner, responsive to the first and the second trackable body orientations can then determine the angular difference between the orientation of the first and the second trackable bodies. The angular difference indicates an angle of rotation of the rotating assembly, utilized to determine the three-dimensional orientation of the isocenter coordinate system. Thus, advantageously, the geometry analyzing program product provides for determining both the position of the isocenter and the orientation of the isocenter coordinate system independent of the angle of rotation of the rotating assembly, using the same predetermined transform matrix.

The geometry analyzing program product also includes a deviation detector, responsive to either of the trackable body position determiner or the isocenter position or both, to detect a deviation in the geometry of the rotating assembly, when so existing. Such deviation indicates a possible isocenter coordinate system definition failure. A deviation responder, responsive to detection of the deviation, correspondingly can respond to such deviation during application of the treatment plan by signaling an existence of the possible isocenter coordinate system definition failure.

More specifically, in an embodiment of the present invention, the isocenter position determiner, can determine a second three-dimensional coordinate position of the isocenter with reference to a fixed trackable body detector offset position through use of a second predetermined transform matrix indicating a transform between a trackable body detector reference coordinate system for the trackable body detector and the predetermined isocenter coordinate system of the treatment apparatus. This trackable body detector reference coordinate system including reference offset position is preferably assigned to a portion of the body of the trackable body detector but can be instead assigned to a separate fixedly mounted fixture. In this embodiment, the deviation detector includes an isocenter comparator, which, responsive to the first and the second determined three-dimensional coordinate positions of the isocenter, compares the first and the second three-dimensional coordinate positions of the isocenter. A substantial difference between the first and the second determined three-dimensional coordinate positions of the isocenter indicates a possible isocenter coordinate system definition failure. Additionally, the isocenter comparator, responsive to the first and the second determined orientations of the isocenter coordinate system, can also compare the first and the second orientations of the isocenter coordinate system. A substantial difference between the first and the second determined orientations of the isocenter coordinate system correspondingly can also indicate a possible isocenter coordinate system definition failure.

In an alternate embodiment of the present invention, the trackable body position determiner determines a plurality of first trackable body positions located along the rotational path of the rotating assembly. In this embodiment, the deviation detector includes a rotational path comparator, which, responsive to the plurality of determined three-dimensional coordinate trackable body positions and a predetermined rotational path of the rotating assembly, determines if either of the plurality of determined first trackable body positions substantially deviate from a position substantially coincident with the predetermined rotational path of the rotating assembly. Such deviation also can indicate a possible isocenter coordinate system definition failure.

Embodiments of the present invention also include a computer readable medium that is readable by a computer to monitor a geometry of an apparatus having one or more rotating assemblies, such as, for example, a patient treatment apparatus. Advantageously, the monitoring can be accomplished during testing of the apparatus or "on the fly" during patient treatment delivery, without the necessity of interrupting the treatment delivery. For example, in an embodiment of the present invention the computer readable medium includes a program product that comprises a set of instructions that, when executed by the computer, cause the computer to perform the operations of: receiving a plurality of position signals produced by a trackable body detector, the signals indicating a separate three-dimensional coordinate position of a plurality of preferably optically trackable indicators connected respectively to a trackable body, which is connected to the rotating assembly along its rotational path. The instructions also include those to perform the operations of: determining, from the plurality of position signals, a three-dimensional coordinate trackable body position of the trackable body; receiving a predetermined transform matrix indicating a transform between a predetermined trackable body reference coordinate system and a predetermined isocenter coordinate system of the treatment apparatus; and responsive to the determined trackable body position and the predetermined transform matrix, determining a respective three-dimensional coordinate position of the isocenter of the apparatus.

Advantageously, a second trackable body can be connected to the rotating assembly. The second trackable body also has a plurality of separate and spaced-apart trackable indicators. The second trackable body advantageously can maintain a generally constant orientation to provide a preferably vertical reference orientation, useful in determining an orientation of the first and the second trackable bodies. In this embodiment of the present invention, the plurality of position signals produced by the trackable body detector can also indicate separate three-dimensional coordinate positions of the plurality of separate and spaced-apart trackable indicators connected to the second trackable body. Correspondingly, the instructions can also include those to perform the operation of determining from the position signals a first trackable body orientation of the first trackable body and a corresponding second trackable body orientation of the second trackable body. Further, responsive to the first trackable body orientation and the corresponding second trackable body orientation, the instructions can include those to perform the operations of: determining an angular difference between the first and the second trackable body orientations indicating an angle of rotation of the rotating assembly; and determining, in response to the angle of rotation of the rotating assembly, a three-dimensional orientation of the isocenter coordinate system for the treatment apparatus independent of angle of rotation of the rotating assembly.

The computer readable medium can also include a set of instructions that, when executed by the computer, cause the computer to perform the operations of: receiving a second predetermined transform matrix indicating a transform between a trackable body detector reference coordinate system for the trackable body detector and the predetermined isocenter coordinate system of the treatment apparatus; determining a second three-dimensional coordinate position of the isocenter referenced to a fixed trackable body detector offset position, responsive to the second predetermined transform matrix; and comparing the first and the second three-dimensional coordinate positions of the isocenter. A substantial difference between the first and the second determined three-dimensional coordinate positions of the isocenter can be indicative of a possible isocenter coordinate system definition failure. Advantageously, knowledge of a potential failure in the definition of the isocenter coordinate system can allow an operator of an apparatus such as, for example, a radiation treatment apparatus, to verify the functionality of the monitored rotating assembly.

In an alternative embodiment of the present invention, the instructions can also include those to perform the operations of: receiving a data set defining a predetermined rotational path of the rotating assembly, to define a rotational path dataset; and responsive to the plurality of determined trackable body positions and the rotational path dataset, determining if the determined trackable body position or positions substantially deviate from a position substantially coincident with the predetermined rotational path of the rotating assembly. Such deviation is indicative of a possible isocenter coordinate system definition failure. The instructions can also include those to perform the operation of determining, in response to the deviation, a corrected three-dimensional coordinate position of the isocenter and orientation of the isocenter coordinate system.

In an embodiment of the present invention, the computer readable medium includes a set of instructions that, when executed by the computer, cause the computer to perform the operations of: receiving a plurality of position signals produced by a trackable body detector, the signals indicating a separate three-dimensional coordinate position of a plurality of separate and spaced-apart trackable indicators connected to a trackable body that is positioned along a rotational path of a rotating assembly; and responsive to the plurality of position signals, determining during patient treatment delivery a three-dimensional coordinate trackable body position of the trackable body. The instructions also include those to perform the operations of: receiving a predetermined transform matrix indicating a transform between a predetermined trackable body reference coordinate system and a predetermined isocenter coordinate system of the treatment apparatus; and responsive to the determined three-dimensional coordinate position of the trackable body and the predetermined transform matrix, determining a respective three-dimensional coordinate position of the isocenter. The instructions can further include those to perform the operations of: detecting a deviation in the geometry of the rotating assembly, when so existing, from the determined three-dimensional coordinate position of the isocenter, such deviation indicating a possible isocenter coordinate system definition failure; and responsive to detection of such deviation, responding to the deviation by signaling an existence of the potential isocenter coordinate system definition failure. Advantageously, such knowledge can allow an operator, during the radiation treatment delivery, to interrupt radiation treatment delivery to prevent either over treating or under treating a target tissue structure and to prevent excessive radiation delivery to a non-target tissue structure.

Embodiments of the present invention also include a method of determining an isocenter of a treatment apparatus having at least one rotating assembly so that a treatment plan can be more accurately applied to a patient. For example, in an embodiment of the present invention, a method includes the step of determining a three-dimensional coordinate position of a first trackable body connected to a preselected portion of one of the rotating assemblies and located at a predetermined position offset relative to a predetermined (physical) three-dimensional coordinate position of an isocenter of the treatment apparatus. The first trackable body has a plurality of separate and spaced-apart indicators each connected at a separate preselected position on the first trackable body to indicate a separate three-dimensional coordinate position of each indicator of the plurality of indicators, so as to provide three-dimensional positional data of the first trackable body. Having determined the three-dimensional coordinate position of the first trackable body, the three-dimensional coordinate position of the isocenter can be determined by applying to the determined three-dimensional position of the first trackable body a predetermined transform matrix indicating a transform between a predetermined first trackable body reference coordinate system and a predetermined isocenter coordinate system positioned coincident with the physical three-dimensional coordinate position of the isocenter. Note, determining the three-dimensional coordinate system definition of the isocenter corresponding to the physical three-dimensional coordinate position of the isocenter is generally referred to as a "calibrating procedure."

Because the first trackable body is connected to a rotating assembly, by its nature, it has an orientation that varies with the rotation of the rotating assembly. Correspondingly, the orientation of the isocenter coordinate system rotates along with the first trackable body relative to the non-rotating portions of the treatment apparatus and treatment room. The actual preselected orientation of the isocenter coordinate system, however, is fixed relative to the non-rotating portions of the treatment apparatus and treatment room. Thus, an embodiment of the present invention, advantageously, provides the operator the ability to determine the three-dimensional orientation of the isocenter coordinate system for the treatment apparatus, independent of angle of rotation of the rotating assembly. This can be accomplished by applying an isocenter angular correction factor, which relates to an angle of rotation of the respective rotating assembly, to the determined three-dimensional orientation of the isocenter coordinate system.

In order to determine the angle of rotation of the rotating assembly and the isocenter correction factor, a second trackable body can be utilized. The second trackable body has a proximal body end portion pivotally connected to or adjacent the first trackable body and a free moving distal body end portion. A medial body portion is connected to and extends between the proximal body end portion and the distal body end portion. Having a pivotally connected proximal body end portion and a free-moving distal body end portion allows the second trackable body to maintain a substantially constant reference orientation. A second plurality of separate and spaced-apart indicators are each connected at a separate preselected position on the second trackable body to indicate a separate three-dimensional coordinate position of each indicator of the second plurality of indicators, to thereby provide second trackable body orientation data of the second trackable body.

The angular rotation of the rotating assembly along with the isocenter angular correction factor can then be determined by first determining an orientation of both the first and the second trackable bodies and then comparing the orientations to ascertain the angular difference. By applying the isocenter angular correction factor to the determined three-dimensional orientation of the isocenter coordinate system, the orientation of the isocenter coordinate system can then be determined independent of angle of rotation of the rotating assembly.

Embodiments of the present invention also include methods of monitoring a geometry of a treatment apparatus having at least one rotating assembly so that a treatment plan can be more accurately applied to a patient. For example, in an embodiment of the present invention, the method includes the steps of: connecting a trackable body to a preselected portion of a rotating assembly located at a predetermined offset position relative to a predetermined three-dimensional coordinate position of an isocenter of the treatment apparatus; and detecting a deviation, when so existing, in the geometry of a rotating assembly of the treatment apparatus by analyzing and sampling at least one position of the trackable body along a rotational path of a rotating assembly to verify a definition of the isocenter coordinate system used by a trackable body tracking apparatus, determined with reference to the trackable body. The method also includes the step of responding to detection of the deviation, when so existing, during application of the treatment plan by signaling an existence of a potential isocenter coordinate system definition failure.

More particularly, a deviation can be detected by determining a first determined three-dimensional coordinate position of the isocenter and/or orientation of the isocenter coordinate system referenced to the trackable body, determining a second three-dimensional coordinate position of the isocenter and/or orientation of the isocenter coordinate system referenced to a fixed trackable body detector offset position of a trackable body detector, and comparing the first and the second determined three-dimensional coordinate positions of the isocenter and/or determined first and second orientations of the isocenter coordinate system. A substantial difference between the first and the second determined three-dimensional coordinate positions of the isocenter or first and second determined orientations of the isocenter coordinate system is indicative of a possible isocenter coordinate system definition failure. Also, a deviation can be detected by determining a plurality of three-dimensional coordinate trackable body positions for the trackable body located along the rotational path of the rotating assembly, and comparing the determined three-dimensional coordinate trackable body positions to a predetermined rotational path of the rotating assembly. A substantial deviation of either of the plurality of determined three-dimensional coordinate trackable body positions from a position substantially coincident with the predetermined rotational path of the rotating assembly is indicative of a possible isocenter coordinate system definition failure.

Advantageously, embodiments of the present invention may negate the requirement for a specific quality assurance check to determine if inadvertent changes have occurred in the calibrated position of a calibrated tracking system indicating the isocenter of the isocenter coordinate system. The embodiments of the present invention can utilize a trackable assembly which can be fixedly positioned in relationship to a predetermined isocenter position to continuously indicate the location and orientation of the isocenter coordinate system. Conveniently, the trackable assembly can be mounted to the radiation delivery or treatment apparatus at a very near distance in relation to the physical isocenter position, making it viewable substantially throughout the treatment delivery. Advantageously, negated is the requirement for a stable or in any other way precisely calibrated camera or optical detection/tracking system or apparatus, the trackable assembly, rather than the camera or optical detection/tracking system or apparatus, can act as a fixture with respect to the physical isocenter position. Advantageously, however, in an embodiment of the present invention, when the trackable system or apparatus is precisely calibrated to the isocenter position, the system is overspecified, and provides the operator verification of the definition of the isocenter coordinate system. Advantageously, embodiments of the present invention can include multiple trackable bodies to provide for all six degrees of freedom of the various rotating assemblies and the patient target (e.g. target tumor) while indicating the location of the isocenter and orientation of the isocenter coordinate system. The continuous position and orientation availability, during radiation delivery, of the trackable assembly and/or other trackable bodies allows for continuous, instantaneous measurement and verification of the tracking system's definition of the isocenter and/or orientation of the isocenter coordinate system as well as the continuous, instantaneous verification of the position and orientation of all items being tracked.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Successful therapy treatments, such as, for example, radiation therapy, rely on the ability to accurately locate and define a radiation beam. The spatial position of the radiation beam is defined by the physical geometry of the treatment apparatus. The geometry of rotating assemblies of the treatment apparatus define a coordinate system of the treatment apparatus, which is used by a therapist to determine the position of the radiation beam and the positioning of the patient. The origin of this coordinate system is referred to as "isocenter" and this coordinate system is referred to as the "isocenter coordinate system." Many treatment systems rely on the accuracy of a calibrated tracking system to reliably indicate the isocenter coordinate system during radiation delivery. These systems are, however, vulnerable to inadvertent changes in that calibrated position. For example, the "camera" or trackable body detector of a typical trackable body tracking system or apparatus is structurally removed from the treatment apparatus by a great distance and fixedly connected to a wall or ceiling mount, and thus, is affected by even slight movements in the camera/detector mounting. Thus, advantageously, as illustrated in FIGS. 1-12, embodiments of the present invention provide a system, apparatus, trackable assembly, program product, and methods for monitoring the geometry of a rotating assembly of the treatment apparatus to determine the correctness of the definition of the isocenter coordinate system used by a trackable body tracking system or apparatus.

Figure 1:
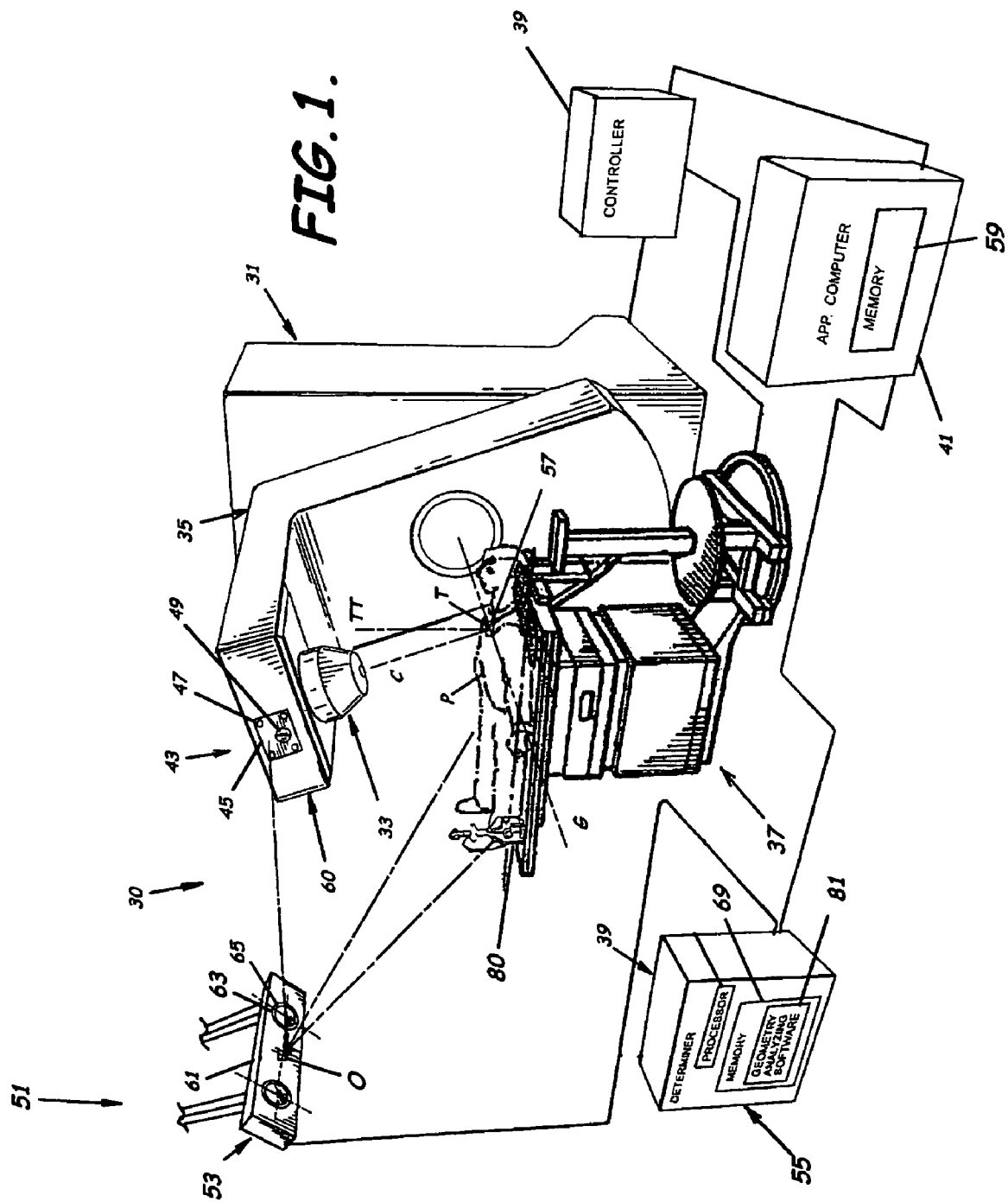
FIG. 1 is a perspective view of a system to monitor a geometry of a treatment apparatus according to an embodiment of the present invention.

As perhaps best shown in FIG. 1, the system 30 generally includes a treatment apparatus having one or more rotating assemblies, such as, for example, a linear accelerator 31. The following discussion will refer to linear accelerator 31 shown in FIG. 1 for illustrative purposes, only. Other treatment apparatus known to those skilled in the art, including but not limited to a magnetic resonance imaging ("MRI") or computerized tomography ("CT") scan device, are also within the scope of the present invention. The linear accelerator 31 has a rotating beam collimator assembly 33 which functions as a radiation emitter, a rotating gantry assembly 35, and a rotating treatment table assembly 37, each preferably controlled by a controller 39. The system 30 also includes an application computer 41 which provides treatment delivery instructions to the controller 39. The system 30 also further includes a trackable assembly 43 connected to the rotating gantry assembly 35. The trackable assembly 43 (see also FIG. 2) includes a fixedly connected first trackable body 45, having a plurality of indicators 47 positioned thereon, which functions as a reference fixture. The trackable assembly 43 also can include a pivotally connected second trackable body 49, also having a plurality of indicators 47 positioned thereon, which provides data used to determine rotation angle of the rotating gantry assembly 35. The system 30 also includes a system or apparatus 51 to track a trackable body which includes a trackable body detector 53 provided to detect a position of the indicators 47, and a determiner 55, in communication with the trackable body detector 53, to determine the position and/or orientation of the first and the second trackable bodies 45, 49. The determiner 55 further determines the location the isocenter 57 of the isocenter coordinate system and can determine rotational path data about the rotating gantry assembly 35.

More specifically, in an embodiment of the present invention, the system 30 includes a treatment apparatus, such as linear accelerator 31, which delivers radiation to a target T in a patient P. The linear accelerator 31 has a plurality of rotating assemblies including: a rotating beam collimator assembly 33, which functions as a radiation emitter; a rotating gantry assembly 35, which positions the radiation beam; and a rotating treatment patient table assembly 37, which positions a patient P. Together the rotating assemblies function to direct a radiation beam through a target T of the patient P. Each rotating assembly has a rotational path in a distinct plane and an axis of rotation. An application computer 41, having a memory 59 and a treatment plan stored in the memory 59, provides treatment delivery instructions to the linear accelerator 31. The rotating gantry assembly 35 has a gantry axis of rotation G and a gantry head 60 positioned adjacent the gantry rotational outer circumference to direct a radiation beam toward the center of the gantry axis of rotation G, in accordance with signals from the controller 39. The rotating beam collimator assembly 33 is connected to and directed by the gantry head 60. The rotating beam collimator assembly 33 generates a radiation beam along a beam axis C and, depending upon the configuration, can shape the profile of the radiation beam. The rotating patient treatment table assembly 37 has a treatment table axis of rotation TT and is positioned adjacent the gantry assembly 35 to move the position of the target T of the patient P with respect to the isocenter 57 before and during treatment. The axis of rotation G of the rotating gantry assembly 35 generally intersects with the beam axis C at a three-dimensional coordinate which defines the isocenter 57 (origin) of the isocenter coordinate system of the linear accelerator 31.

As shown in FIGS. 1-4, the system 30 includes a subsystem or apparatus to track the trackable body, hereinafter referred to as a "trackable body tracking apparatus" 51. The trackable body tracking apparatus 51 includes a preferably optical trackable body detector or camera subsystem, such as, for example, trackable body detector 53, and a determiner 55. The trackable body detector 53 includes a detector body 61 positioned spaced apart from the linear accelerator or other treatment apparatus and trackable assembly 43. The trackable assembly 43 is positioned to be viewed/detected by the trackable body detector 53. The trackable assembly 43 includes a first trackable body 45 fixedly connected to a preselected portion of the rotating gantry assembly 35 at a predetermined offset position relative to a predetermined three-dimensional coordinate system definition of the isocenter 57 and along the rotational path RP (FIG. 4) of the rotating gantry assembly 35. The first trackable body 45 has a plurality of separate and spaced-apart indicators 47 each connected at a separate preselected position thereon to indicate to the trackable body detector 53 separate three-dimensional coordinate positions of each indicator 47 of the plurality of indicators 47. The indicators 47 are preferably in the form of passive indicators such as, for example, retro-reflective spheres, which advantageously provide upwards of a 180-degree reflective field of view and decrease inherent wiring requirements associated with active indicators. Note, the indicators 47 can, however, be in other forms including that of active emitters.

The trackable body detector 53 is preferably an optical detector or camera locator subsystem, such as, for example, the camera or opti-electrical motion measurement system, known as the Polaris®, by Northern Digital Inc., Ontario Canada, having a pair of optical receivers 63, each with a field of view and adapted to receive optical energy emitted or reflected by each of the plurality of indicators 47 when positioned in the field of view. In this form, the receivers 63 can detect the three-dimensional sphere position of each of the plurality of indicators 47 of the trackable assembly 43 when positioned simultaneously within the field of view of both of the optical receivers 63 to produce the plurality of position signals. When the plurality of indicators 47 are in the form of optical retro-reflective spheres, the detector 53 can include a pair of illuminators, such as, infrared illuminators 67, each separately positioned adjacent one of the receivers 63, to selectively illuminate each of the plurality of indicators 47 when positioned in the field of view of the respective adjacent receiver 63.

Figure 3:
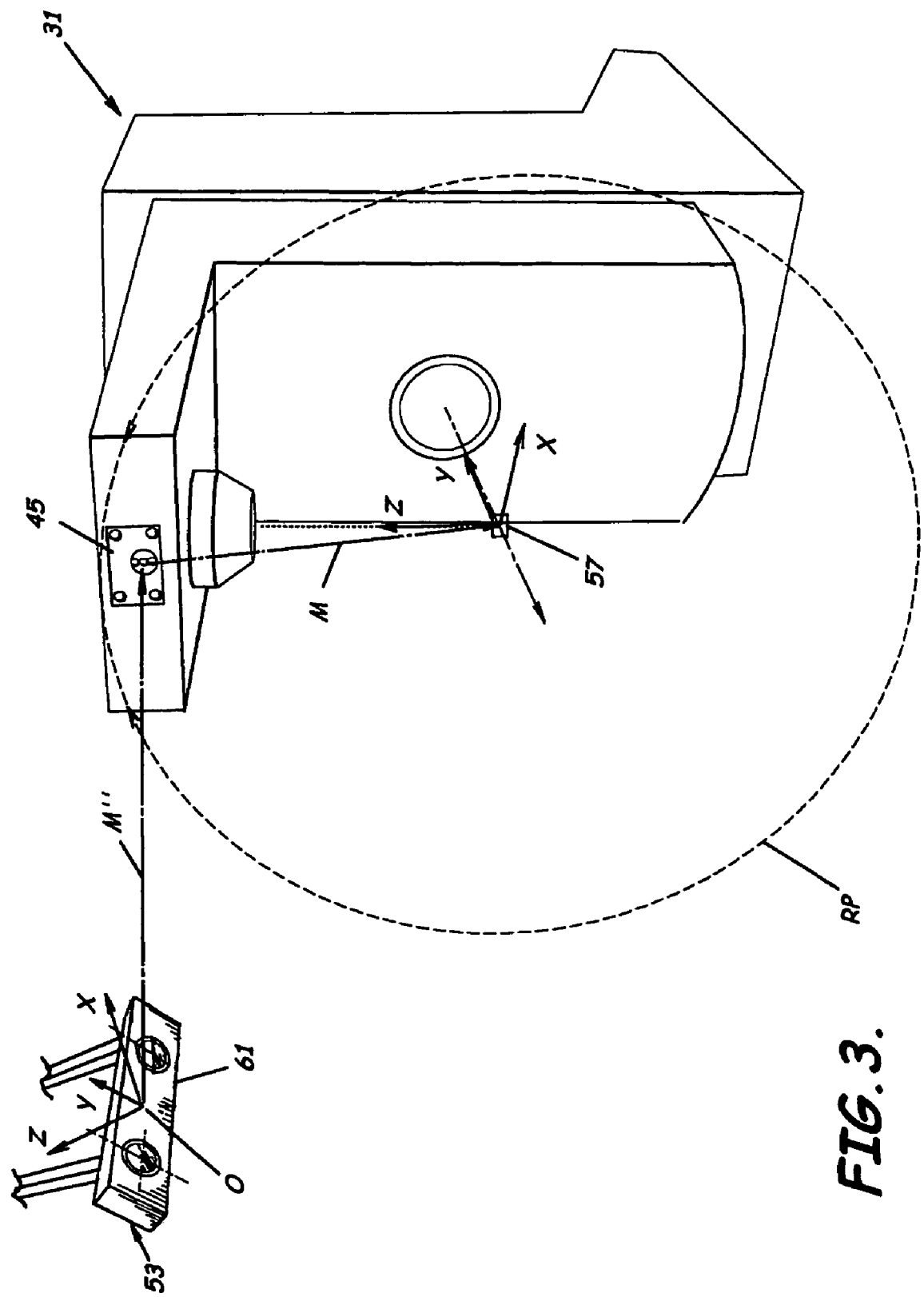
FIG. 3 is a perspective view of a portion of a system to monitor a geometry of a treatment apparatus illustrating determining a position of an isocenter of the treatment apparatus according to an embodiment of the present invention.

Referring to FIGS. 1 and 3, the determiner 55 communicates with the trackable body detector 53 to receive and process the plurality of position signals produced by the trackable body detector 53. The determiner 55 can determine (in trackable body tracking apparatus/camera space) the three-dimensional coordinate system definition of the isocenter 57 referenced to the first trackable body 45 through use of a predetermined transform matrix M (FIG. 3) preferably stored in the memory 69 of the determiner 55. As further shown in FIG. 3, the trackable body tracking apparatus 51 has a preselected trackable body detector coordinate system illustrated on the face of detector body 61. The preselected trackable body detector coordinate system, having an preselected origin and orientation, can be established in a fixed relationship with the trackable body detector 53 to define a trackable body detector offset position O. Note, transform matrix M indicates a mathematical construct which can be used to relate or transform the location (position) and orientation of a coordinate system relative to some other coordinate system. The transform matrix M is preferably in the form of what is referred to as a 4-by-4 matrix. Such transformation matrix defines a set of three rotations (to the new orientation), and a set of three translations (to the new position). Transformation matrices can be chain together in order to relate the location and orientation of a coordinate system to a successive series of coordinate systems. Note also, the term "location" or "position" with respect to isocenter generally specifies the x, y, and z coordinates of the isocenter. The term "orientation" with respect to isocenter specifies direction vectors of the coordinate axes of the isocenter coordinate system.

In the preferred embodiment of the present invention, the trackable body detector 53 detects the first trackable body 45, which functions as a reference fixture to the isocenter 57 and isocenter coordinate system. The determiner 55 then determines a transform matrix M" between an assigned trackable body reference coordinate system preferably centered upon the trackable body detector offset position O and a reference coordinate system preferably centered upon the determined position of the first trackable body 45. The determiner 55 can receive or retrieve the predetermined transform matrix M, which provides or indicates a transform between a first trackable body reference coordinate system centered upon a first trackable body position of the first trackable body 45 (normally coincident with the illustrated location of the first trackable body 45) and isocenter coordinate system centered upon the physical three-dimensional coordinate position of the isocenter 57. Along with transform matrix M", the determiner 55 is provided sufficient data to transform the three-dimensional coordinate system definition of the isocenter 57 to detector/camera space. When properly calibrated to the trackable body detector 53, the first trackable body 45 provides a ready reference to the three-dimensional coordinate position of the isocenter 57. Note, the determination of the three-dimensional coordinate system definition of the isocenter 57 in trackable body detector/camera space is generally referred to as calibrating the trackable body tracking apparatus 51 to a location in space of the physical three-dimensional coordinate position of the isocenter 57 and orientation of the isocenter coordinate system.

Because the system definition of the first trackable body 45 with respect to the trackable body detector offset position O of the trackable body detector 53 can be readily determined, the three-dimensional coordinate position (location and/or orientation) of the detector body 61 need not remain in a highly stable position, required where reference to the three-dimensional coordinate system definition of the isocenter 57 is determined solely with respect to the trackable body detector offset position O. That is, the detector 53 can advantageously be readily moved without losing reference to the isocenter 57 because, rather than the detector 53 performing the function of a reference fixture, the first trackable body 45 provides a relative reference to the isocenter 57. Further, having such a reference fixture, especially one positioned close to the isocenter 57, provides additional significant advantages. The greater the distance between the trackable body detector 53 and the isocenter 57, the less accurate the trackable body tracking apparatus 51. Still further, advantageously, the first trackable body 45 allows the trackable body detector 53 to be positioned in a less intrusive location and with a less stable mounting than would otherwise be required for merely determining and maintaining reference to the isocenter 57.

Figure 4:
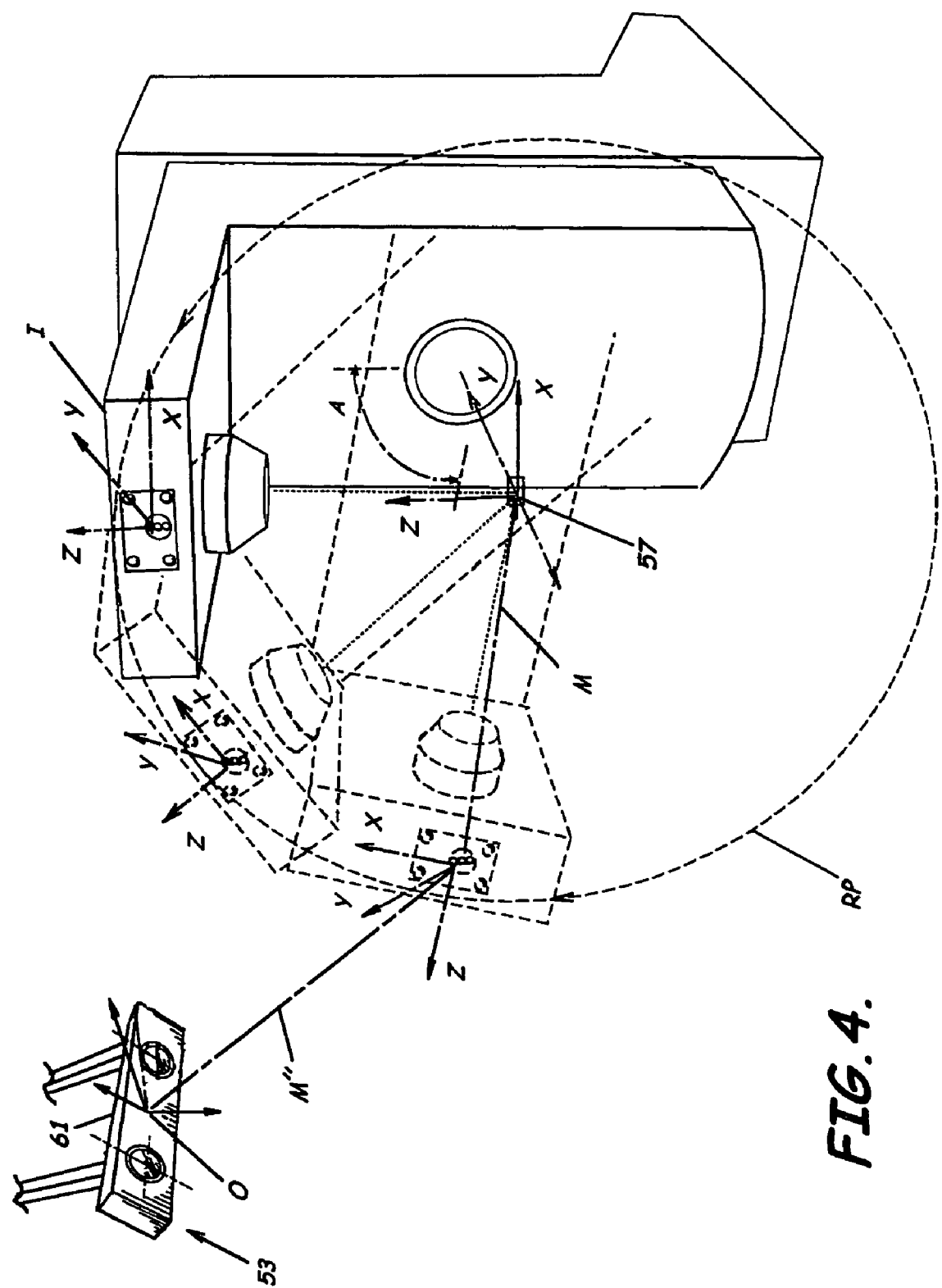
FIG. 4 is a perspective view of a portion of a system to monitor a geometry of a treatment apparatus illustrating determining a position and an orientation of an isocenter of the treatment apparatus according to an embodiment of the present invention.

As perhaps best shown in FIG. 4, because the first trackable body 45 is connected to a rotating assembly, such as the rotating gantry assembly 35, it should be readily apparent that transform matrix M maintains a reference to the isocenter 57 that will appear to rotate with the rotation of the rotating gantry assembly 35. The orientation of the isocenter coordinate system conceptually rotates along with the first trackable body 45 relative to the non-rotating portions of the treatment apparatus (linear accelerator 31) and the treatment room. The physical isocenter 57 and corresponding preselected orientation of the isocenter coordinate system, however, remains stationary and does not rotate with the rotation of the rotating gantry assembly 35 relative to the non-rotating portions of the treatment apparatus and treatment room. Thus, the first trackable body 45 can generally only be used to produce a reference to the isocenter 57 having coordinate system axes oriented relative to the orientation of the first trackable body 45 at the time the determination is made. Thus, advantageously, in an embodiment of the present invention, the trackable assembly 43 can also include a second trackable body 49 either connected to the first trackable body 45 (as illustrated) or separately connected to a preferably adjacent preselected portion of the rotating gantry assembly 35. The second trackable body 49 can be utilized to determine or to correct the relative orientation of the isocenter coordinate system determined with reference to the first trackable body 45 when the rotating gantry assembly 35 is rotated off an initial reference position, illustrated as position I.

Figure 2:
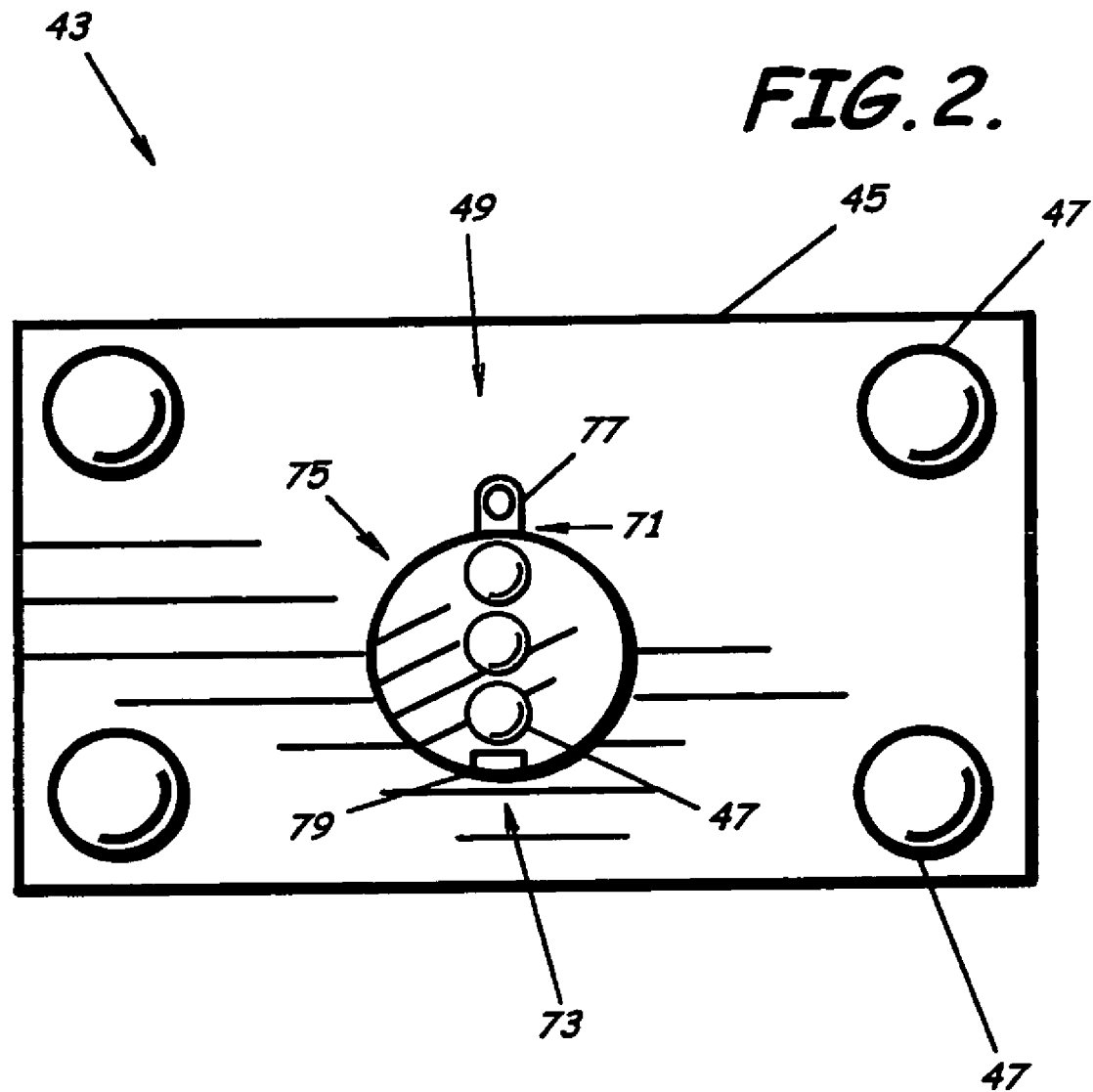
FIG. 2 is a perspective view of a trackable assembly according to an embodiment of the present invention.

To this end, and as perhaps best shown in FIG. 2, the second trackable body 49 has a proximal body end portion 71 which, rather than being fixedly mounted, can be pivotally connected to either the rotating gantry assembly 35, or to or adjacent the first trackable body 45. The second trackable body 49 also has a free-moving distal body end portion 73 and a medial body portion 75 connected to and extending between the proximal body end portion 71 and the distal body end portion 73. Similar to the first trackable body 45, the medial body portion 75 of the second trackable body 49 can have a plurality of separate and spaced-apart indicators, such as indicators 47, each connected at a separate preselected position of the second trackable body 49, also to indicate to the trackable body detector 53 a three-dimensional coordinate position of each indicator 47. This pivoting-proximal end/free-distal end configuration can provide a pendulum-type action, which, responsive to gravity, allows the second trackable body to maintain a constant orientation (illustrated as vertical) used by the determiner 55 as a reference orientation.

To provide such pendulum-type action and to maintain a substantially constant orientation during rotation of the rotating gantry assembly 35, the second trackable body 49 can be connected to a preferably non-trackable mount 77 which can include dampeners (not shown), known and understood by those skilled in the art, to prevent excess undesirable oscillations. The second trackable body 49 can be appropriately weighted with a weight or weights 79 to synergistically maintain the second trackable body 49 in a substantially constant orientation during rotation of the rotating gantry assembly 35. Advantageously, in the illustrated embodiment of the trackable assembly 43, the body of the first trackable body 45 has a flat configuration which can allow the second trackable body 49 to freely rotate within the confines of the first trackable body 45 without obstructing any of the indicators 47 carried by the first trackable body 45, while maintaining a close profile to the rotating assembly.

The above described reference orientation provided by the second trackable body 49 allows the determiner 55 to correct or adjust the relative orientation of the isocenter coordinate system which was determined with reference to the first trackable body 45. This incorrect orientation is the result of a rotational error typically existing when the rotating gantry assembly 35 carrying the trackable assembly 43 is rotated off its initial reference position I (FIG. 3), illustrated as vertical. More specifically, to determine the orientation of the isocenter coordinate system, the determiner 55 first determines the orientations of the first and the second trackable bodies 45, 49, respectively. The determiner 55 can then determine the rotation angle of the first trackable body 45, which relates to the rotational position of the rotating gantry assembly 35 from the initial reference position I. This can be accomplished by determining an angular difference in orientation between the first and the second trackable bodies 45, 49. The correct orientation of the isocenter coordinate system can be determined by conceptually rotating the reference orientation of the isocenter 57, determined from the first trackable body 45, by an amount related to the angular difference between the respective orientations of the first and the second trackable bodies 45, 49. Thus, advantageously an accurate reference orientation (and position) of the isocenter coordinate system can be provided (determined) using the same predetermined transform matrix M regardless of the rotational orientation of the first trackable body 45, which can vary due to rotation of the rotating gantry assembly 35.

Figure 5:
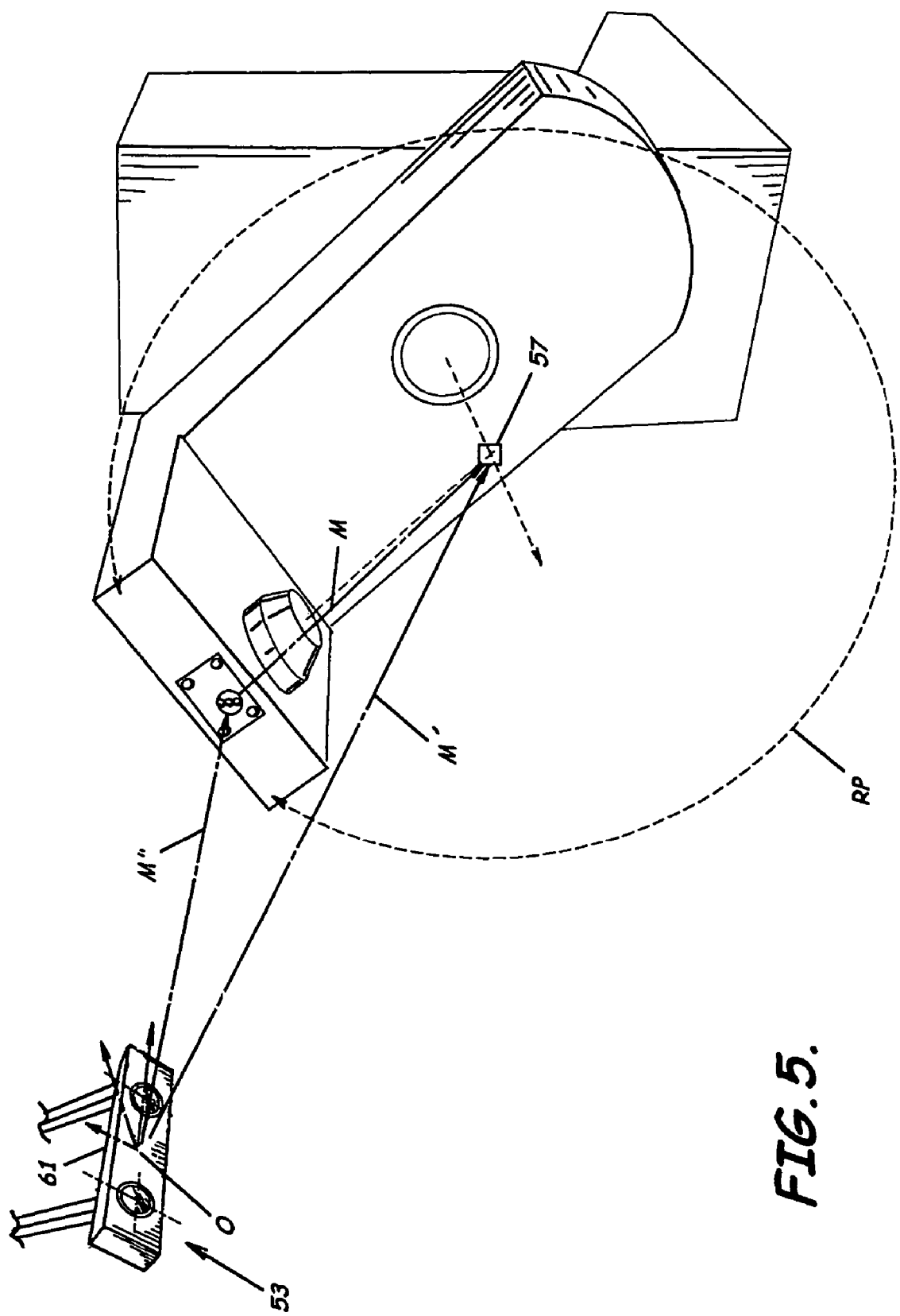
FIG. 5 is a perspective view of a portion of a system to monitor a geometry of a treatment apparatus illustrating multiple methods of determining the isocenter of the treatment apparatus according to an embodiment of the present invention.
Figure 6:
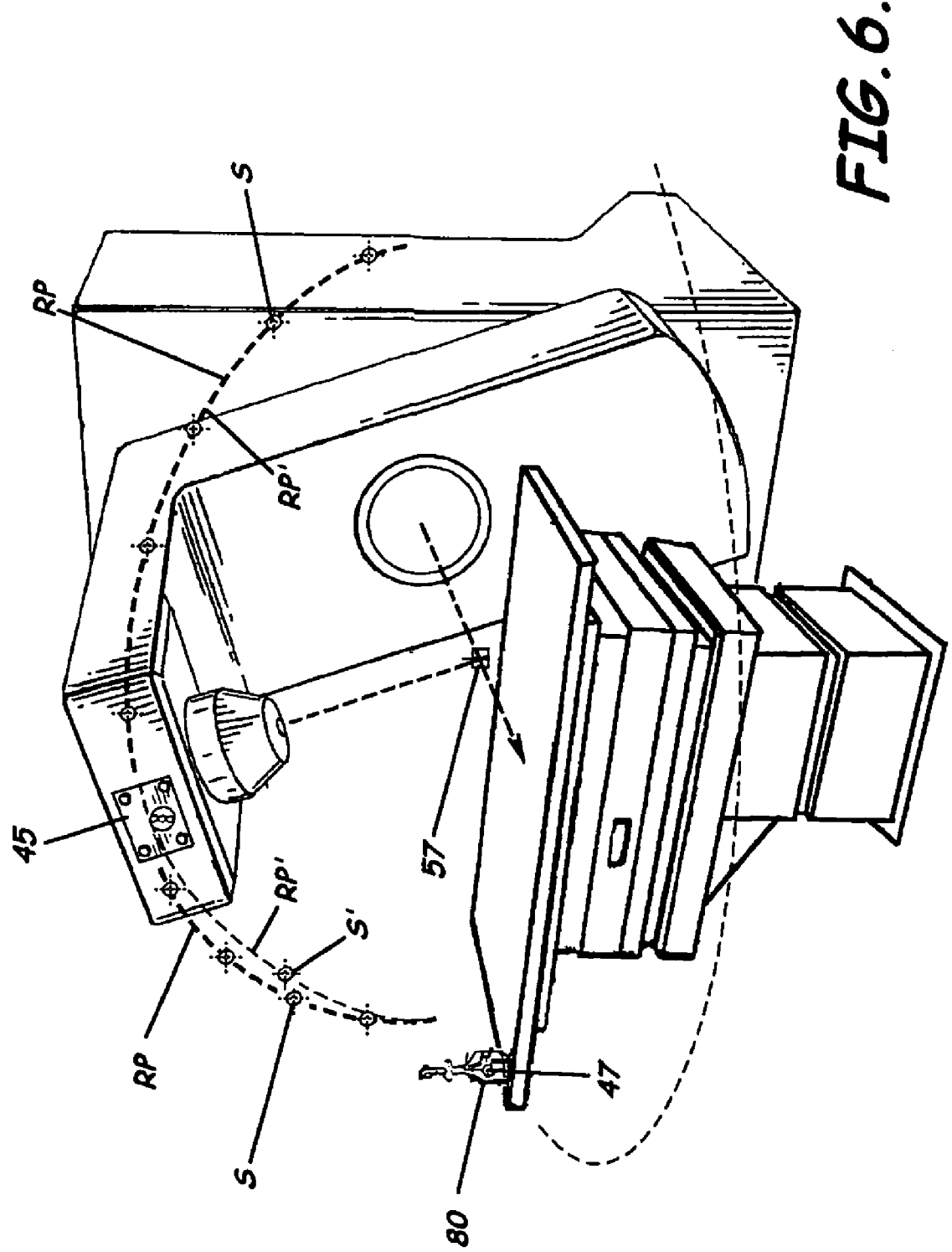
FIG. 6 is a perspective view of a treatment apparatus illustrating a rotational path of a rotating assembly having imperfections according to an embodiment of the present invention.

As shown in FIGS. 5 and 6, in an embodiment of the present invention, the determiner 55 can also detect or determine a possible isocenter coordinate system definition failure, when so existing. To do so, as shown in FIG. 5, a trackable body detector reference coordinate system including trackable body detector reference offset position, such as offset position O, can be selected to "over specify" the system 30. This allows for separate and independent determinations of isocenter 57 to be made, one with reference to a fixture (e.g. trackable body 45) positioned on the rotating gantry assembly 35 (e.g. trackable body 45), the other reference to an immobilized fixture normally associated with the body 61 of the detector 53.

For example, the determiner 55, through use of a second predetermined transform matrix M', can make a second independent determination of the three-dimensional coordinate system definition of the isocenter 57 but with reference to the trackable body detector reference offset position O, rather than with reference to the trackable body reference position of the first trackable body 45. The second predetermined transform matrix M', preferably also stored in the memory 69 of the determiner 55, can provide or indicate a transform between the trackable body detector reference coordinate system (normally coincident with offset position O) and the isocenter coordinate system (normally coincident with the physical three-dimensional coordinate position of the isocenter 57). The separately determined three-dimensional coordinate positions of the isocenter 57 can then be compared. A substantial difference would indicate a possible isocenter coordinate system definition failure. Note, the transform matrices are shown in the form of an arrow between the trackable body detector 53 and trackable body 45 and the trackable body 45 and isocenter 57 pointing towards isocenter 57 for illustrative purposes only. The transform of the various coordinate systems can be accomplished in either direction.

Note, although the possible isocenter coordinate system definition failure is generally due to an unexpected undesired movement of either the trackable body 45 or the trackable body detector 53 caused by mounting failure, the possible isocenter coordinate system definition failure can be caused by a misalignment or partial failure of the rotating assembly. Note also, although in the preferred embodiment of the present invention the preselected trackable body detector reference coordinate system is preferably assigned coincident with a location of a portion of the body 61 of the trackable body detector 53 (as illustrated), it can be instead assigned to a separate immobilized trackable fixture (not shown) that is stationery with respect to the treatment apparatus and treatment room. This configuration would allow for "over-specifying" the system 30 without the requirement to immobilize the trackable body detector 53. This alternative configuration minimizes inaccuracies due to movement of the trackable body detector 53 caused by wall-vibrations or other external stimulus. Further, this alternative allows for positioning a fixture that is smaller and that is less likely to need maintenance, and thus, is less likely to be inadvertently moved or needed to be moved.

As an alternative methodology of detecting or determining a possible isocenter coordinate system definition failure, as shown in FIG. 6, the determiner 55 can determine a plurality of sampled two or three-dimensional coordinate first trackable body positions S along the rotational path RP of the rotating gantry assembly 35. The determined positions S provide current rotational path data that can be compared to a predetermined rotational path RP' of the rotating gantry assembly 35, typically referred to as a "quality assurance (QA) circle," preferably stored in the memory 69 of the determiner 55, in the form of a rotational path dataset. Thus, the determiner 55 can determine if either of the plurality of determined first trackable body positions S substantially deviate from a position (e.g. illustrated position S') substantially coincident with the predetermined rotational path RP' of the rotating gantry assembly 35. Such deviation would be indicative of a possible isocenter coordinate system definition failure.

In an embodiment of the present invention, the determiner 55 can respond to such detection or determination of a deviation before or during application of a treatment plan to the patient P by signaling an existence of the potential isocenter coordinate system definition failure. Further, in an embodiment of the present invention, where the determiner 55 is in communication with application computer 41, the application computer 41 can notify an operator a deviation exists, signal the controller 39 of the treatment apparatus to terminate treatment delivering, and/or where the treatment apparatus is in a form such as that of a linear accelerator 31, signal the controller 39 to adjust radiation beam direction or intensity as necessary to compensate for the deviation. Additionally, in response to such deviation, the determiner 55 can project a re-calculated three-dimensional coordinate system definition of the isocenter 57 from the first trackable body 45 regardless of the angle of rotation A (FIG. 4) of the rotating gantry assembly 35.

Still further, in an embodiment of the present invention, the system 30 can include a third trackable body which can provide patient position data. For example, in an embodiment of the present invention, a trackable body 80 (FIG. 6) having a plurality of separate and spaced apart indicators 47 mounted thereto, such as, for example, that disclosed in U.S. patent application Ser. No. 10/957,128 by Smetak et al., titled "System and Tracker for Tracking an Object, and Related Methods" or a suitable substitute, can be connected to a preselected portion of the rotating treatment table assembly 37 at a predetermined offset position relative to the target T of the patient P. In this embodiment of the present invention, in response to the detection of a deviation, the determiner 55 can determine the position of the target T to enable the application computer 41 to signal the controller 39 to, if authorized to do so, adjust the position of the rotating treatment table assembly 37 to move the target T to coincide with a corrected three-dimensional coordinate system definition of the isocenter 57.

Figure 7:
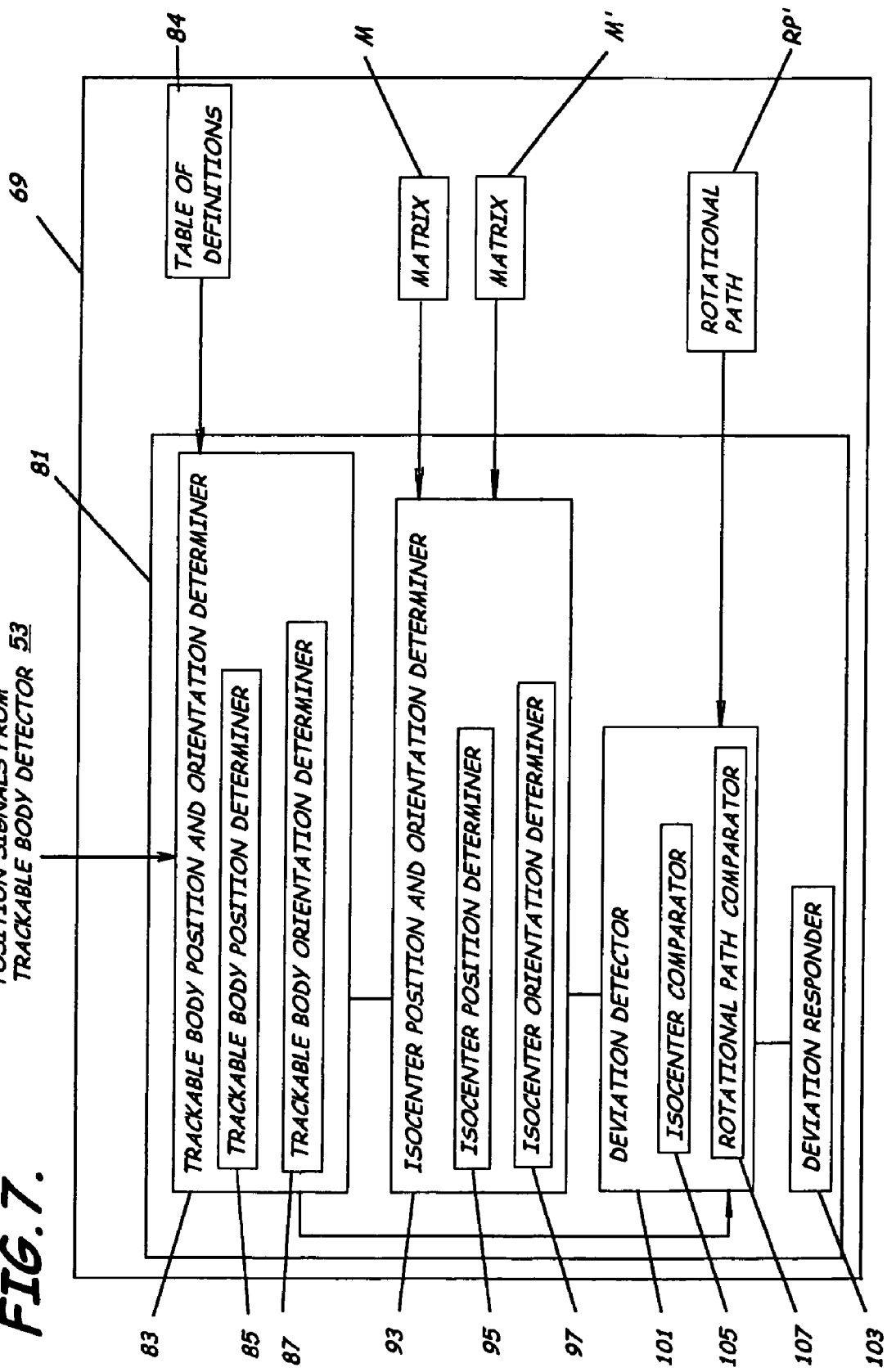
FIG. 7 is a schematic diagram of program product to monitor a geometry of a treatment apparatus according to an embodiment of the present invention.

As shown in FIG. 7, the function of the determiner 55 can be implemented in hardware and/or software/program product, however, in the preferred embodiment of the present invention, the function of the determiner 55 is implemented almost entirely in software/program product either preloaded in memory 69 of the determiner 55 or contained on separate storage media, such as, for example, a compact disc, portable hard drive, a remote computer, etc. Correspondingly, the system 30 can further include a program product, such as geometry analyzing program product 81, to analyze treatment apparatus geometry. Note, the program product 81 can be in the form of microcode, programs, routines, and symbolic languages that provide a specific set or sets of ordered operations that control the functioning of the hardware and direct its operation, as known and understood by those skilled in the art. Note also, the determiner 55 is illustrated for simplicity as a single separate unit (FIG. 1), and the geometry analyzing program product 81 is described below as positioned within memory 69 of the determiner 55.

The determiner 55, however, is actually preferably implemented such that it is distributed over the trackable body detector 53 and the illustrated determiner 55, or in a remote computer (not shown). Correspondingly, all or a portion of the geometry analyzing program product 81 can be located in both the trackable body detector 53 and the determiner 55, and/or partially or solely in a remote computer (not shown). In fact, in the preferred embodiment of the invention, the geometry program product 81 is at least partially located in the trackable body detector 53. Thus, the physical embodiment of the trackable detector 53 also can include a portion of the physical and the functional embodiment of the determiner 55. To this end, the illustrated trackable body detector 53 typically includes its own processor and memory (not shown).

As shown in FIG. 7, the geometry analyzing program product 81 includes a trackable body position and orientation determiner 83 having a trackable body position determiner 85, which can determine the position of a trackable body, and a trackable body orientation determiner 87, which can determine the orientation of a trackable body, both of which can be in the form of a unitary module or separate modules. When loaded in memory 69 of the determiner 55, the trackable body position and orientation determiner 83 is positioned to receive and is responsive to the plurality of position signals produced by a trackable body detector 53 which indicate separate three-dimensional coordinate positions of a plurality of separate and spaced-apart trackable indicators 47.

The trackable body position and orientation determiner 83 can identify the first and the second trackable bodies 45, 49, and relate their respective trackable indicators 47 to a preselected coordinate system assigned to each respective trackable body 45, 49. This can be accomplished through use of a table of definitions 84 stored in memory 69 or through means of another suitable trackable body identifier, known to those skilled in the art. The result is to identify the first and the second trackable bodies 45, 49, and to determine a three-dimensional coordinate trackable body position and/or orientation of the first and the second trackable bodies 45, 49.

The plurality of indicators 47 for the first and the second trackable bodies 45, 49, can be positioned on the respective bodies 45, 49, so that each have unique segment lengths between each other indicator 47. This positioning allows the trackable body tracking apparatus 51 to uniquely identify each preselected trackable body when viewed by the trackable body detector 53. As such, the plurality of indicators 47 of the respective trackable bodies 45, 49, can be positioned with respect to a selected origin of a coordinate system assigned to or preselected for the respective trackable bodies 45, 49 (see e.g. FIG. 4). This geometry can allow the trackable body position and orientation determiner 83 to determine a three-dimensional coordinate position for the origin and linear direction (direction vectors) of the each axes of the coordinate system separately assigned to trackable bodies 45, 49, which can be used to define the position and the orientation of the preselected trackable bodies 45, 49. Other methodologies of defining position and orientation, however, known by those skilled in the art, are within the scope of the present invention.

The geometry analyzing program product 81 includes an isocenter position and orientation determiner 93 which can function as a single integrated module or separate modules including an isocenter position determiner 95, which can determine the position of the isocenter 57, and an isocenter orientation determiner 97, which can determine the orientation of the isocenter 57, both of which can also be in the form of a unitary module or separate modules. The isocenter position and orientation determiner 93 is responsive to the determined three-dimensional coordinate position of the first trackable body 45 and a first predetermined transform matrix M (FIGS. 3 and 4) to determine a first three-dimensional coordinate position of the isocenter 57. Note, as stated previously, the predetermined transform matrix M indicates a transform between the first trackable body reference coordinate system of the first trackable body 45 on the rotating assembly (rotating gantry assembly 35) and a predetermined/preselected isocenter coordinate system of the treatment apparatus (e.g. linear accelerator 31).

As shown in FIGS. 4 and 7, in an embodiment of the present invention having the previously described second trackable body 49, the orientation of the isocenter coordinate system can also be readily determined. The isocenter position and orientation determiner 93, responsive to the determined orientations for the first and the second trackable bodies 45, 49, can determine the angular difference between the determined orientations. The angular difference indicates both an angle of rotation A (FIG. 4) of the rotating gantry assembly 35 from an initial position I (FIG. 4) and an isocenter angular correction factor, which can be utilized to determine the three-dimensional orientation of the isocenter coordinate system. Thus, advantageously, the geometry analyzing program product 81 can provide for determining both the position the isocenter 57 and the orientation of the isocenter coordinate system with reference to various positions along the rotating gantry assembly 35, independent of angle of rotation A of the rotating gantry assembly 35, using the same predetermined transform matrix M.

As shown in FIG. 7, the geometry analyzing program product 81 also can include a deviation detector 101 which can detect a deviation in geometry of a rotating assembly, such as, rotating gantry assembly 35, indicative of a potential isocenter coordinate system definition failure. Note, as stated previously, the deviation can result from a malfunction or unexpected movement in the rotating assembly carrying the first trackable body 45, though, it is most typically a result of improper movement of the first trackable body 45 or the trackable body detector 53. A deviation responder 103 can respond to detection of such deviation before or during application of a treatment plan to the patient P by signaling an existence of a potential isocenter coordinate system definition failure. In an embodiment of the present invention, where the determiner 55 is in communication with application computer 41 (FIG. 1), the application computer 41 can notify an operator a deviation exists, signal the controller 39 of the treatment apparatus to terminate treatment delivering, and/or where the treatment apparatus is in a form such as that of a linear accelerator 31, signal the controller 39 to adjust radiation beam direction or intensity or, if provided authorization, reposition the rotating treatment table assembly 37, as necessary, to compensate for the deviation.

As shown in FIGS. 5 and 7, in an embodiment of the present invention, the isocenter position and orientation determiner 93 can receive a second predetermined transform matrix M', also preferably stored in memory 69, to determine a second determined three-dimensional coordinate position of the isocenter 57, but instead with reference to the fixed trackable body detector offset position O. Note, as stated previously, the predetermined transform matrix M' preferably indicates a transform between the predetermined isocenter coordinate system and a trackable body detector reference coordinate system, which normally is coincident with offset position O.

The trackable body detector reference offset position is preferably assigned to the trackable body detector 53 or alternatively assigned to an immobilized non-rotating (static) fixture (not shown) positioned in view of the trackable body detector 53 and in view of the physical isocenter coordinate position of the isocenter 57. In this embodiment of the present invention, the deviation detector 101 includes an isocenter comparator 105, which can receive the first and the second determined three-dimensional coordinate positions of the isocenter 57, determined as described above, and can compare the first and the second three-dimensional coordinate positions of the isocenter 57. A substantial difference between the first and the second determined three-dimensional coordinate positions of the isocenter 57 indicates a possible isocenter coordinate system definition failure. The isocenter comparator 105 can also compare the first and the second orientations of the isocenter coordinate system. A substantial difference between the first and the second determined orientations of the isocenter coordinate system correspondingly can also indicate a possible isocenter coordinate system definition failure. The above described comparison can be made either separately or in combination with the comparison of a difference between the first and the second determined three-dimensional coordinate positions/system definitions of the isocenter 57.

As shown in FIGS. 6 and 7, in an embodiment of the present invention, the trackable body position and orientation determiner 93 can determine a plurality of three-dimensional coordinate trackable body positions S located along the rotational path RP of the rotating gantry assembly 35. In this embodiment, the deviation detector 101 can include a rotational path comparator 107, which compares the plurality of determined trackable body positions S with a predetermined rotational path RP' of the rotating gantry assembly 35, preferably in the form of a dataset, to determine if either of the plurality of determined first trackable body positions S substantially deviate from a position substantially coincident with the predetermined rotational path RP' of the rotating gantry assembly 35 (e.g. position S'). Such deviation indicates a possible isocenter coordinate system definition failure.

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include but are not limited to: nonvolatile, hard-coded type media such as read only memories (ROMs), CD-ROMs, and DVD-ROMs, or erasable, electrically programmable read only memories (EEPROMs), recordable type media such as floppy disks, hard disk drives, CD-R/RWs, DVD-RAMs, DVD-R/RWs, DVD+R/RWs, flash drives, and other newer types of memories, and transmission type media such as digital and analog communication links.

As shown in FIGS. 1-12, embodiments of the present invention also include a computer readable medium that is readable by a computer to monitor the geometry of an apparatus having one or more rotating assemblies. For example, again referencing the linear accelerator 31 (FIG. 1) for illustrative purposes, a trackable body 45 is connected to a portion of the rotating gantry assembly 35 along a rotational path of the rotating gantry assembly 35. A plurality of preferably optically trackable indicators 47 is connected to the trackable body 45 to provide positional data for the optically trackable indicators 47. A trackable body tracking apparatus 51 includes a trackable body detector 53 provided to detect a position of each of the indicators 47, and a determiner 55, in communication with the trackable body detector 53. The determiner 55, a combination of the detector 53/determiner 55, or a remote computer (not shown), can perform the function of the computer to monitor the geometry (one or more rotating assemblies 33, 35, 37, of the linear accelerator 31). Advantageously, such monitoring can be accomplished either prior to or during patient treatment delivery.

In this embodiment of the present invention, the computer readable medium includes a program product having a set of instructions that, when executed by a computer, cause the computer to perform the operations of: receiving a plurality of position signals produced by the trackable body detector 53. As perhaps best shown in FIG. 3, the instructions also include those to perform the operations of: determining, from the plurality of position signals, a three-dimensional coordinate trackable body position of the trackable body 45; receiving a predetermined transform matrix M indicating a transform between a trackable body reference coordinate system of the trackable body 45 and a predetermined isocenter coordinate system of the apparatus (e.g. linear accelerator 31); and responsive to the determined trackable body position of the trackable body 45 and the predetermined transform matrix M, determining a respective three-dimensional coordinate system definition of the isocenter 57 of the linear accelerator 31. This determination can be accomplished during testing of the linear accelerator 31, or "on the fly" during patient treatment delivery, without the necessity of interrupting the treatment delivery.

A second trackable body 49 can be connected to the rotating gantry assembly 35. The second trackable body 49 also has a plurality of separate and spaced-apart trackable indicators, such as, indicators 47. The second trackable body 49 advantageously maintains a generally constant orientation to provide a preferably vertical reference orientation useful in determining an orientation of the first and the second trackable bodies 45, 49. In this embodiment of the present invention, the plurality of position signals produced by the trackable body detector 53 can also indicate separate three-dimensional coordinate positions of the plurality of separate and spaced-apart trackable indicators 47 of the second trackable body 49. Correspondingly, the instructions can also include those to perform the operation of determining from the position signals a first trackable body orientation of the first trackable body 45 and a corresponding second trackable body orientation of the second trackable body 49. Further, responsive to the first trackable body orientation and the corresponding second trackable body orientation, the instructions can include those to perform the operations of: determining an angular difference between the first and the second trackable body orientations (FIG. 4) to define an isocenter coordinate system angular correction factor, which relates to an angle of rotation A (FIG. 4) of the rotating gantry assembly 35; and determining, in response to either the angular correction factor or the angle of rotation A, a preferably three-dimensional orientation of the isocenter coordinate system for the linear accelerator 31 independent of an angle of rotation A of the rotating gantry assembly 35.

The computer readable medium can also include a set of instructions that, when executed by the computer, cause the computer to perform the operations of: receiving a second predetermined transform matrix M' (FIG. 5) indicating a transform between a trackable body detector reference coordinate system for the trackable body detector 53, normally a position coincident with offset position O (FIG. 5), and the predetermined or preselected isocenter coordinate system of the linear accelerator 31; and responsive to the second predetermined transform matrix M', independently determining a second three-dimensional coordinate position of the isocenter 57 referenced to the trackable body detector 53 (e.g. offset position O).

The instructions can also include those to perform the operations of comparing the first and the second three-dimensional coordinate positions of the isocenter 57 A substantial difference between the first and the second determined three-dimensional coordinate positions of the isocenter 57 can be indicative of a possible isocenter coordinate system definition failure. Further, the instructions can also include those to perform the operations of: independently determining a second orientation of the isocenter coordinate system corresponding to the second determined three-dimensional coordinate position of the isocenter 57, and comparing the first and the second determined orientations of the isocenter coordinate system. A substantial difference between the first and the second determined orientations of the isocenter coordinate system can also be indicative of a possible isocenter coordinate system definition failure.

Advantageously, knowledge of a potential failure in the coordinate system definition of the isocenter 57 can allow an operator of a treatment apparatus, such as, for example, the linear accelerator 31, to verify the functionality of the monitored rotating assembly prior to treatment delivery, and can allow the operator during the radiation treatment delivery, to interrupt radiation treatment delivery to prevent either over treating or under treating a target tissue structure T (FIG. 1) and to prevent excessive radiation delivery to a non-target tissue structure.

Further, the instructions can also include those to perform the operation of: determining a differential between the determined orientation of the first trackable body 45 and the corresponding determined orientation of the second trackable body 49 at a location (an angular position) of the first trackable body 45 with respect to the rotating gantry assembly 35 (FIG. 4) coinciding with the potential isocenter coordinate system definition failure. The instructions also include those to perform the operations of: determining from the comparison, the angular position; and responsive to the determined angular position of the first trackable body 35, determining a location of the cause of the possible isocenter coordinate system definition failure.

In an alternative embodiment of the present invention, the instructions can include those to perform the operations of: receiving a data set defining a predetermined rotational path PR' of the rotating gantry assembly 35, to define a rotational path dataset; and responsive to the plurality of determined trackable body positions S and the rotational path dataset, determining if one of the determined trackable body position or positions S substantially deviate from a position (illustrated as S') substantially coincident with the predetermined rotational path RP' of the rotating gantry assembly 35. Such deviation is indicative of a possible isocenter coordinate system definition failure. The instructions can also include those to perform the operation of determining, in response to the determined or detected deviation, a corrected three-dimensional coordinate position of the isocenter 57 and orientation of the isocenter coordinate system.

Figure 8:
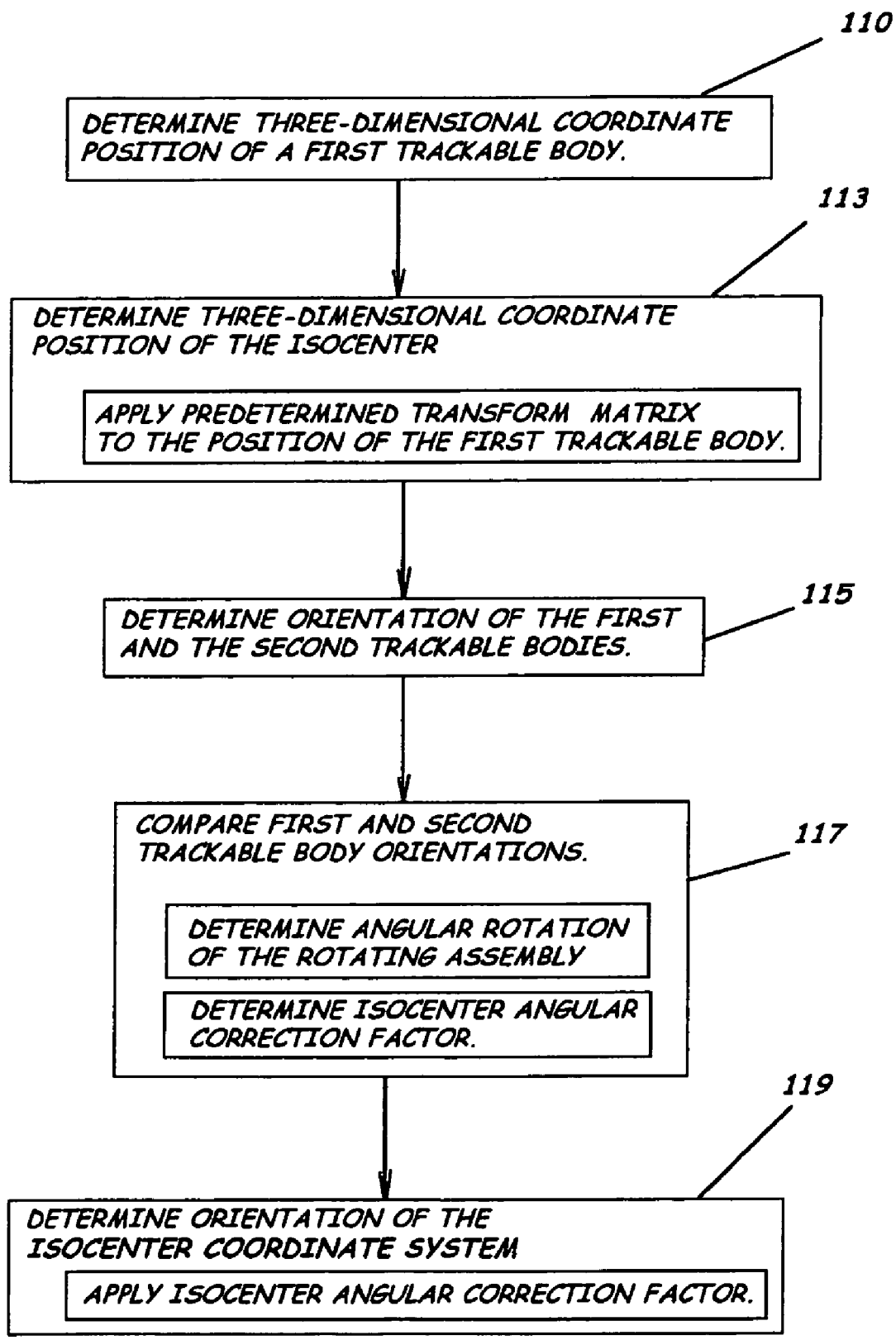
FIG. 8 is a flow chart of a method to monitor a geometry of a treatment apparatus illustrating determining an isocenter of the treatment apparatus according to an embodiment of the present invention.

As shown in FIGS. 4 and 8, embodiments of the present invention also include a method of determining a coordinate system definition of an isocenter 57 of a treatment apparatus, such as linear accelerator 31, having at least one rotating assembly so that a treatment plan can be more accurately applied to a patient P (FIG. 1). For example, in an embodiment of the present invention a method includes the step of determining (block 110) a three-dimensional coordinate position (location and/or orientation) of a first trackable body 45 connected to a preselected portion of one of the rotating assembly, such as, for example, rotating gantry assembly 35, and located at a predetermined trackable body reference position offset relative to a predetermined (physical) three-dimensional coordinate position of an isocenter 57 of the linear accelerator 31. The first trackable body 45 has a set of a plurality of separate and spaced-apart indicators, such as indicators 47, each connected at a separate preselected position thereon to indicate a separate three-dimensional coordinate position of each indicator 47 in the set of the plurality of indicators 47, so as to provide three-dimensional positional data of the first trackable body 45. Having determined the three-dimensional coordinate position of the first trackable body 45, the three-dimensional coordinate system definition of the isocenter 57 can be readily determined (block 113) by applying a predetermined transform matrix M indicating a transform between a coordinate system of the first trackable body 45 and the isocenter coordinate system. Note, determining the three-dimensional coordinate system definition of the isocenter 57 is generally referred to as a calibrating procedure whereby a physical location of the isocenter 57 and orientation of the isocenter coordinate system is converted into an electronic location usable by an application computer 41 to formulate and deliver a treatment plan.

Because the first trackable body 45 is connected to a rotating assembly, by its nature, it has an orientation that varies with the rotation of the rotating assembly 35. Thus, in an embodiment of the present invention, the three-dimensional orientation of the isocenter coordinate system for the linear accelerator 31 is determined independent of angle of rotation A of the rotating gantry assembly 35 by applying to the determined three-dimensional coordinate position and relative orientation of the isocenter coordinate system, provided by the first trackable body 45, an isocenter angular correction factor, which is related or equivalent to the angle of rotation A. In order to determine the isocenter correction factor, a second trackable body 49 can be pivotally connected preferably to or adjacent the first trackable body 45. The second trackable body 49 has a medial body portion 75 carrying a set of a plurality of separate and spaced-apart indicators, such as indicators 47, each connected at a separate preselected position thereon. The indicators 47 indicate a separate three-dimensional coordinate position of each indicator 47 in the set of the plurality of indicators 47, to thereby provide second trackable body orientation data of the second trackable body 49. Having a pivotally connected proximal body end portion 71 and a free-moving distal body end portion 73 allows the second trackable body 49 to maintain a substantially constant reference orientation, regardless of the angle of rotation A of the rotating gantry assembly 35.

By determining an orientation of the first and the second trackable bodies 45, 49 (block 115), and comparing the orientations (block 117) to ascertain the angular difference, the angle of rotation A of the rotating gantry assembly 35 along with the isocenter angular correction factor can be readily determined. The orientation of the isocenter coordinate system can then be determined (block 119) independent of angle of rotation A of the rotating gantry assembly 35 by applying the isocenter angular correction factor to the three-dimensional coordinate position of the isocenter 57 having an orientation determined relative to the orientation of the first trackable body 45. That is, to correctly determine both the position of the isocenter 57 and orientation of the isocenter coordinate system, relative to the non-rotating portion of the linear accelerator and/or treatment room, the orientation of the isocenter coordinate system associated with the position of the isocenter 57 determined relative to the first trackable body 45 is conceptually rotated or "oriented" by an amount related to the angle of rotation A of the rotating gantry assembly 35.

Figure 9:
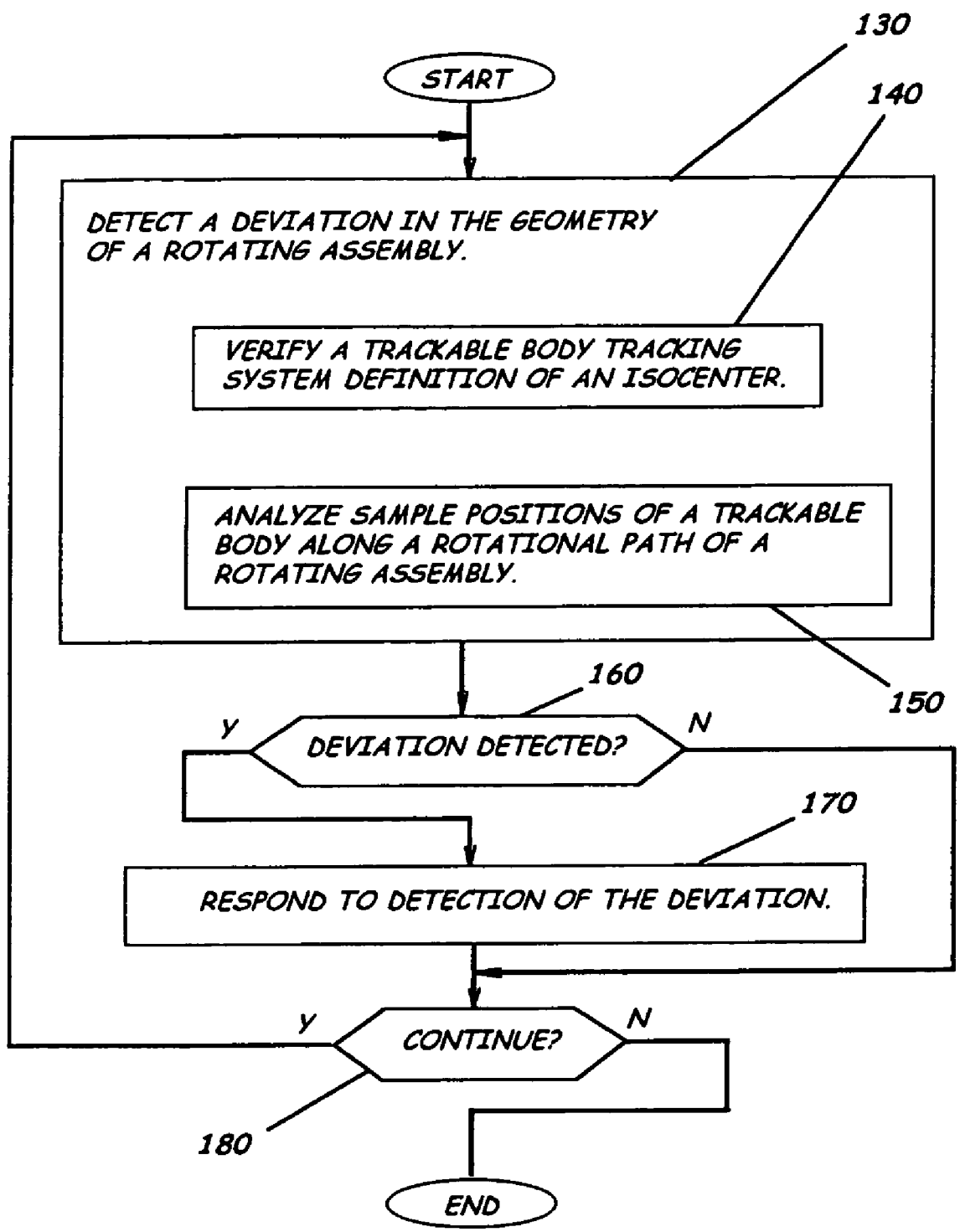
FIG. 9 is a high-level flow chart of a method to monitor a geometry of a treatment apparatus according to an embodiment of the present invention.
Figure 10:
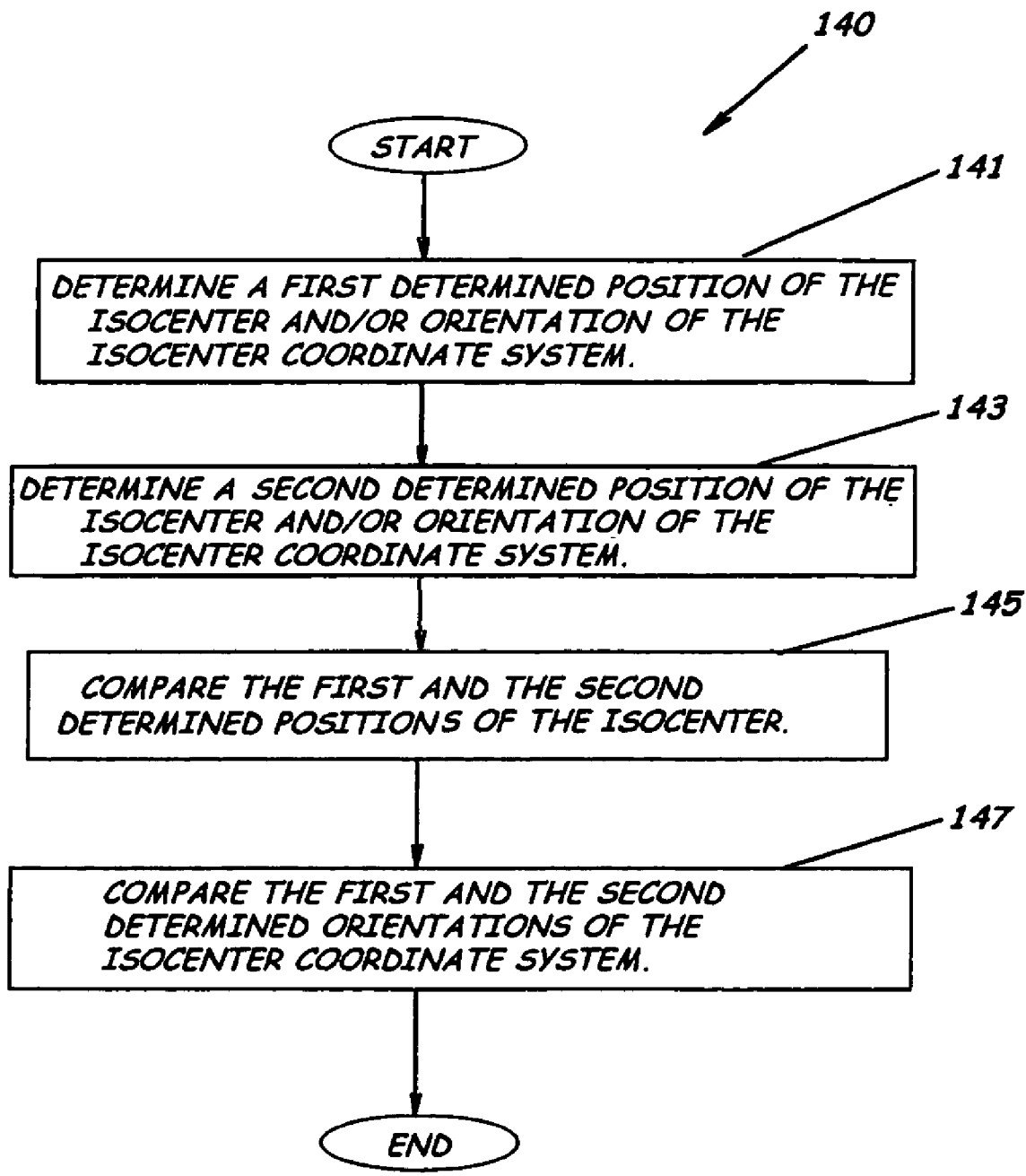
FIG. 10 is a flow chart of a method to monitor a geometry of a treatment apparatus illustrating steps to verify a definition of an isocenter coordinate system according to an embodiment of the present invention.
Figure 11:
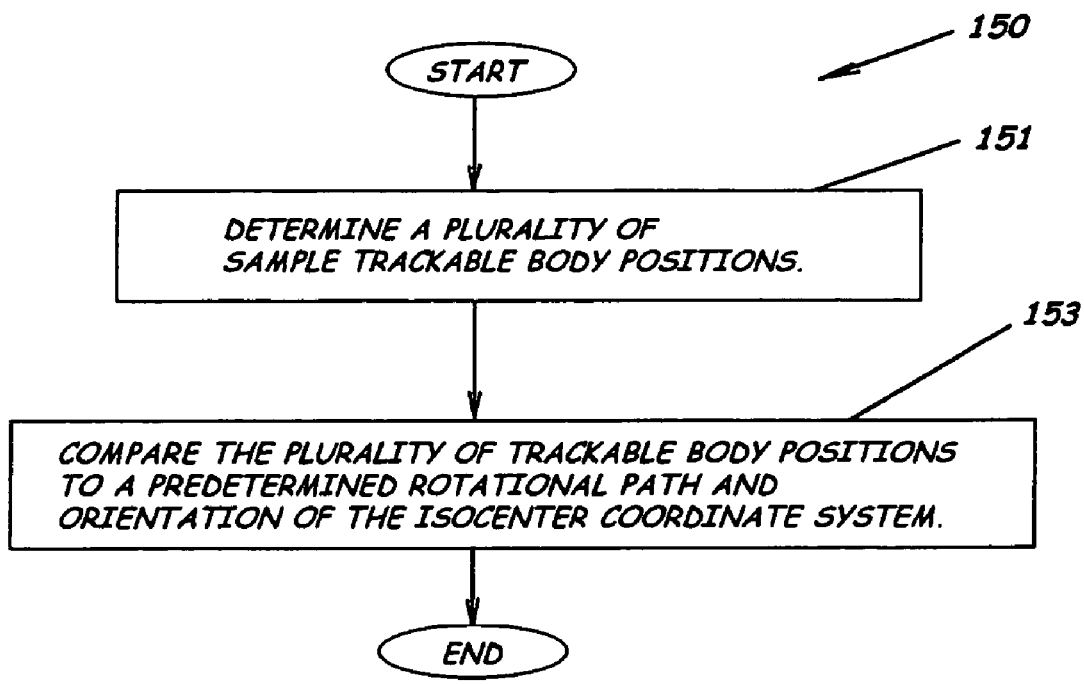
FIG. 11 is a flow chart of a method to monitor a geometry of a treatment apparatus illustrating steps to analyze sample positions of a trackable body along a rotational path of a rotating assembly rotating assembly according to an embodiment of the present invention.

As shown in FIGS. 9-11, embodiments of the present invention also include methods of monitoring a geometry of a treatment apparatus, such as linear accelerator 31, having at least one rotating assembly, such as, rotating gantry assembly 35, so that a treatment plan can be more accurately applied to a patient. For example, in an embodiment of the present invention, the method includes the step of detecting a deviation (block 130), when so existing, in the geometry of a rotating assembly of a treatment apparatus, such as linear accelerator 31, and, if a deviation is detected (block 160), responding to such detected deviation (block 170).

As shown in FIGS. 4-6, and 9-12, the step of detecting a deviation (block 130) can include either or both of the steps of verifying a definition of an isocenter 57 (block 140) of a trackable body tracking system or apparatus, such as trackable body tracking apparatus 51, determined with reference to the trackable body 45, and/or analyzing sample positions of a preferably optically trackable body (block 150), such as trackable body 45, along a rotational path RP of the rotating gantry assembly 35. In the former, the trackable body 45 is connected to a preselected portion of a rotating gantry assembly 35 and located at a predetermined trackable body position offset relative to a predetermined three-dimensional coordinate position of the isocenter 57 of the linear accelerator 31.

More specifically, as shown in FIGS. 5, 9, and 10, a deviation can be detected by determining a first determined three-dimensional coordinate position of the isocenter 57 and/or orientation of the isocenter coordinate system referenced to a trackable body position and/or orientation of the trackable body 45 (block 141), determining a second three-dimensional coordinate position of the isocenter 57 and/or orientation of the isocenter coordinate system referenced to an immobilized fixture having a location such as, for example, a fixed trackable body detector offset position O of a trackable body detector 53 (block 143), and comparing the first and the second determined three-dimensional coordinate positions of the isocenter 57 (block 145) and/or comparing the first and the second orientations of the isocenter coordinate system (block 147). A substantial difference between the first and the second determined three-dimensional coordinate positions of the isocenter 57 and/or a substantial difference in the first and the second orientations of the isocenter coordinate system indicate a possible isocenter coordinate system definition failure.

Also, as shown in FIGS. 6, 9, and 11, a deviation can alternatively be detected by determining a plurality of two or three-dimensional coordinate trackable body positions S (block 151) for the trackable body 45 located along the rotational path RP of the rotating gantry assembly 35, and comparing (block 153) the determined three-dimensional coordinate trackable body positions S to a predetermined rotational path RP' of the rotating gantry assembly 35, to determine if either of the plurality of determined three-dimensional coordinate trackable body positions S substantially deviate from a position (e.g. position S') substantially coincident with the predetermined rotational path RP' of the rotating gantry assembly 35. Such deviation indicates a possible isocenter coordinate system definition failure.

Figure 12:
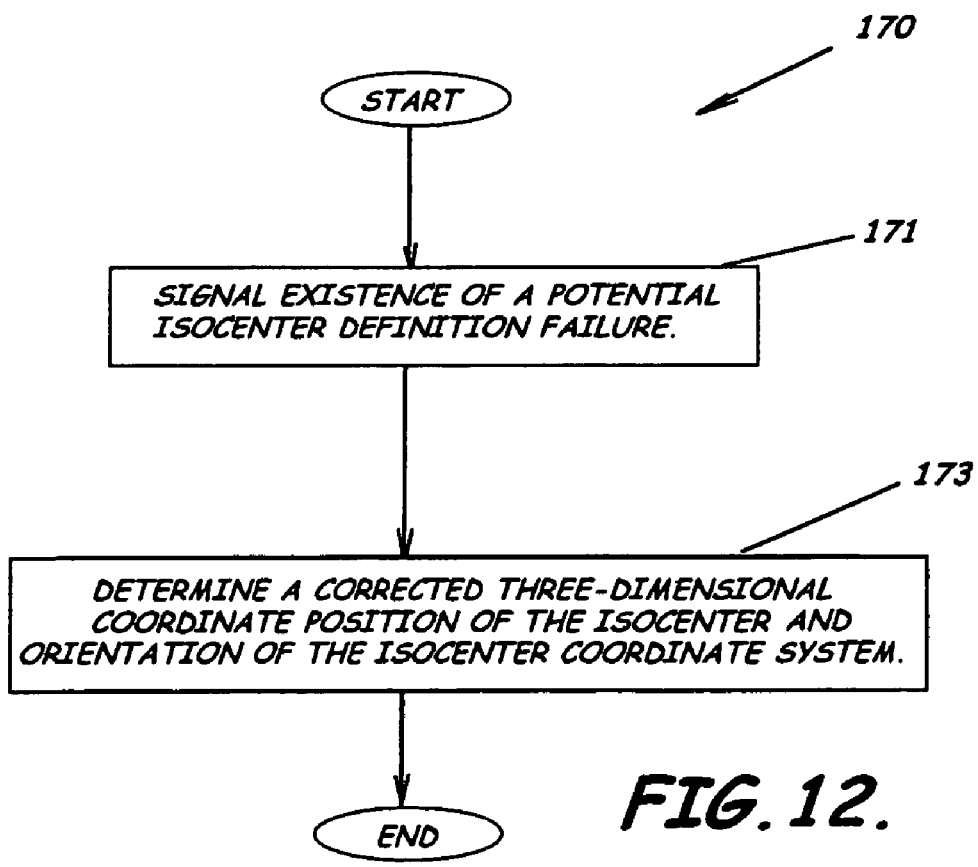
FIG. 12 is a flow chart of a method to monitor a geometry of a treatment apparatus illustrating steps to respond to detection of a deviation in an isocenter coordinate system definition according to an embodiment of the present invention.

As shown in FIGS. 9 and 12, when a deviation is detected (block 160), the method also includes the step of responding to detection of the deviation (block 170). The operator can then either continue or terminate operations (block 180). If the operations are to continue, the geometry of the rotating gantry assembly 35 can continue to be monitored. Advantageously, the operator can be provided various methods of responding to a detected deviation. Prior to or during application of the treatment plan, the step of responding to detection of the deviation (block 170) can be accomplished by signaling an existence of a potential isocenter coordinate system definition failure (block 171) and/or by determining a corrected three-dimensional coordinate position of the isocenter 57 and/or orientation of the isocenter coordinate system (block 173). This allows either an operator, or in the linear accelerator example, an application computer 41, to stop radiation treatment or optionally to adjust the juxtaposition of the radiation beam to the target T by varying the radiation beam shape or intensity or repositioning of the target T by rotating the rotating treatment table assembly 37.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the attached claims. For example, the treatment apparatus was described and illustrated in the form of a linear accelerator. The invention, however, is not limited to such apparatus and can be used with any apparatus having at least one rotating assembly which requires monitoring of the geometry of the apparatus to verify a definition of a coordinate system of the apparatus. Also for example, the determiner was illustrated as a single piece of hardware having memory and geometry analyzing program product, however, the determiner and/or functions of the determiner and the geometry analyzing program product can be installed in the detector, in the illustrated determiner, in both, or in a remote computer. Further, the program product can be independently stored in a mobile storage media, such as, a compact disc, portable hard drive, etc., or be located on separate pieces of storage media for loading on multiple separate components. Further, the constant orientation trackable body was illustrated positioned on the variable orientation trackable body. It can, however, be positioned at various other locations on the rotating assembly. Additionally, the constant orientation trackable body can be implemented using other methodologies known to those skilled in the art to maintain a constant orientation, such as, for example, gyroscopic methodologies.

The invention claimed is:

1. A system to monitor a geometry of a radiation treatment apparatus to monitor a location of an origin and orientation of a coordinate system used to reference radiation beam and patient positioning to thereby detect a possible isocenter coordinate system definition failure so that a treatment plan can be more accurately applied to a patient, the system comprising:

an application computer having a memory associated therewith, and a treatment plan stored in the memory to provide radiation treatment delivery instructions;

a radiation treatment apparatus, in communication with the application computer, to provide radiation treatment to the patient, the radiation treatment apparatus including:
a radiation emitter positioned to emit a radiation beam,
a controller, responsive to the treatment delivery instructions, to control delivery of the radiation beam to the patient, and
a plurality of rotating assemblies each to direct the radiation beam through a target of the patient and each having a rotational path in a distinct plane and an axis of rotation, the axis of rotation of each of the plurality of rotating assemblies intersecting the axis of rotation of each other rotating assembly of the plurality of rotating assemblies at a substantially same three-dimensional coordinate to define an isocenter of an isocenter coordinate system of the treatment apparatus;

a trackable body detector having a detector body positioned spaced apart from the treatment apparatus and having a receiver positioned to receive energy to thereby detect three-dimensional positions and to produce a plurality of position signals indicating three-dimensional coordinate positions;

a trackable assembly positioned to be detected by the trackable body detector and including:
a first trackable body fixedly connected to a preselected portion of the one of the plurality of rotating assemblies at a predetermined first trackable body offset position relative to a predetermined three-dimensional coordinate system definition of the isocenter and along the rotational path of the one of the plurality of rotating assemblies at a preselected angle of rotation, the first trackable body having a first set of a plurality of separate and spaced-apart indicators each connected at a separate preselected position thereon to indicate to the trackable body detector a separate three-dimensional coordinate position of each indicator in the first set of the plurality of indicators, and
a second trackable body having a proximal body end portion pivotally connected to the first trackable body, a free-moving distal body end portion, a medial body portion connected to and extending between the proximal body end portion and the distal body end portion, and having a second set of a plurality of separate and spaced-apart indicators each connected at a separate preselected position of the second trackable body to indicate to the trackable body detector a three-dimensional coordinate position of each indicator in the second set of the plurality of indicators; and a determiner in communication with the trackable body detector and the application computer and comprising:
a memory associated therewith,
a table of definitions stored in the memory and including:
preselected segment lengths between each indicator in the first and the second sets of the plurality of indicators of each respective first and second trackable bodies to identify the first and the second trackable bodies when being detected by the trackable body detector, and
three-dimensional coordinate positions of each indicator in the first and second sets of the plurality of indicators with respect to an origin of a coordinate system preselected for each respective first and second trackable body to thereby identify a three-dimensional coordinate position for the origin and linear direction of the each axes of each respective coordinate system of each respective first and second trackable body, the linear direction of each axes of the preselected coordinate system of the first trackable body defining a first trackable body orientation and the linear direction of each axes of the preselected coordinate system of the second trackable body defining a second trackable body orientation, a predetermined transform matrix stored in the memory to indicate a transform between a preselected first trackable body coordinate system and a predetermined isocenter coordinate system, and geometry analyzing program product stored in the memory, in communication with the application computer, and responsive to the plurality of position signals produced by the trackable body detector to analyze treatment apparatus geometry, the geometry analyzing program product including:

a trackable body position and orientation determiner, responsive to the plurality of position signals produced by the trackable body detector and the table of definitions stored in memory, to determine at least one three-dimensional coordinate first trackable body position and a respective at least one first trackable body orientation of the first trackable body along the rotational path of the one of the plurality of rotating assemblies, and to determine a corresponding at least one second trackable body orientation of the second trackable body, an isocenter position and orientation determiner responsive to the determined at least one first trackable body position, the determined at least one first trackable body orientation, the determined at least one second trackable body orientation, and the predetermined transform matrix stored in memory, to determine a respective at least one three-dimensional coordinate system definition of the isocenter and relative orientation of the isocenter coordinate system, and to determine an angular difference between the at least one first trackable body orientation and a corresponding at least one second trackable body orientation, the angular difference indicating an angle of rotation of the one of the plurality of rotating assemblies, to thereby determine a three-dimensional orientation of the isocenter coordinate system for the treatment apparatus independent of the angle of rotation of the one of the plurality of rotating assemblies, a deviation detector, responsive to at least one of the trackable body position and orientation determiner and the isocenter position and orientation determiner, to detect a deviation in geometry of the at least one of the plurality of rotating assemblies, when so existing, such deviation indicating a possible isocenter coordinate system definition failure, and a deviation responder, responsive to detection of the deviation, to respond to such deviation during application of the treatment plan by signaling the application computer, the application computer positioned to at least one of notify an operator a deviation exists, signal the controller to terminate radiation delivery, and signal the controller to adjust radiation beam direction or intensity to compensate for the deviation.

2. A system as defined in claim 1,
wherein the at least one three-dimensional coordinate first trackable body position determined by the trackable body position and orientation determiner is a plurality of first trackable body positions located along the rotational path of the one of the plurality of rotating assemblies;

wherein the determiner further includes a data set defining a predetermined rotational path of the one of the plurality of rotating assemblies stored in the memory; and wherein the deviation detector of the geometry analyzing program product further includes a rotational path comparator, responsive to the plurality of determined three-dimensional coordinate first trackable body positions, to compare the determined plurality of first trackable body positions to the predetermined rotational path to thereby determine if either of the plurality of determined first trackable body positions substantially deviate from a position substantially coincident with the predetermined rotational path of the one of the plurality of rotating assemblies, such deviation indicating a possible isocenter coordinate system definition failure.

3. A system as defined in claim 2, wherein the isocenter position and orientation determiner, responsive to the determination of the deviation, determines a corrected three-dimensional coordinate system definition of the isocenter and orientation of the isocenter coordinate system.

4. A system as defined in claim 3, wherein the corrected three-dimensional coordinate system definition of the isocenter and orientation of the isocenter coordinate system is determined for a plurality of rotational positions along a maximum rotational range of the one of the plurality of rotating assemblies.

5. A system as defined in claim 1,
wherein the predetermined transform matrix is a first predetermined transform matrix;

wherein the determined at least one three-dimensional system definition of the isocenter is a first determined three-dimensional coordinate system definition of the isocenter determined with reference to the first trackable body position;

wherein the trackable body detector has a preselected trackable body detector reference coordinate system;

wherein the trackable body detector is positioned at a preselected location offset from the three-dimensional coordinate system definition of the isocenter to define a preselected trackable body detector reference offset position of the trackable body detector coordinate system;

wherein the determiner has a second predetermined transform matrix stored in the memory to indicate a transform between the predetermined isocenter coordinate system and preselected trackable body detector reference coordinate system;

wherein the isocenter position and orientation determiner, responsive to the second predetermined transform matrix, determines a second three-dimensional coordinate system definition of the isocenter with reference to the trackable body detector reference offset position; and wherein the deviation detector of the geometry analyzing program product further includes an isocenter comparator, responsive to the first and the second determined three-dimensional coordinate system definitions of the isocenter, to compare the first and the second determined three-dimensional coordinate system definitions of the isocenter, a substantial difference between the first and the second determined three-dimensional coordinate system definitions of the isocenter indicating a possible isocenter coordinate system definition failure.

6. A system as defined in claim 5,
wherein the determined at least one three-dimensional orientation of the isocenter coordinate system is a first determined three-dimensional orientation of the isocenter coordinate system determined with reference to the first trackable body position;
wherein the trackable body detector coordinate system has a preselected orientation to define a preselected trackable body detector reference orientation;
wherein, responsive to the second transform matrix and the preselected trackable body detector reference orientation, the isocenter position and orientation determiner determines a second orientation of the isocenter coordinate system with reference to the preselected trackable body detector reference orientation; and
wherein the isocenter comparator, responsive to the first and the second determined orientations of the isocenter coordinate system, compares the first and the second determined orientations of the isocenter coordinate system, a substantial difference between the first and the second determined orientations of the isocenter coordinate system indicating a possible isocenter coordinate system definition failure.

7. A system as defined in claim 3,
wherein the at least one of the plurality of rotating assemblies is a rotating gantry assembly;
wherein a second of the plurality of rotating assemblies includes a rotating treatment table assembly;
wherein the system further comprises a third trackable body connected to the rotating treatment table assembly at a predetermined offset position relative to the target of the patient during treatment of the patient, the third trackable body having a third set of a plurality of separate and spaced-apart indicators each connected at a separate preselected position thereon to indicate to the trackable body detector a separate three-dimensional coordinate position for each of the third set of the plurality of indicators;
wherein the trackable body position and orientation determiner, responsive to the plurality of position signals produced by the trackable body detector, determines a three-dimensional coordinate third trackable body position indicating the position of the target of the patient; and
wherein, during treatment, the deviation responder, responsive to detection of the deviation, when so existing, responds to such deviation by signaling the application computer to reposition the rotating treatment table assembly to thereby position the target to coincide with the corrected three-dimensional coordinate system definition of the isocenter.

8. A system to monitor a geometry of a treatment apparatus to thereby detect a possible isocenter coordinate system definition failure, the system comprising:
an application computer having a memory associated therewith, and a treatment plan stored in the memory to provide treatment delivery instructions;
a treatment apparatus, in communication with the application computer, to provide radiation treatment to the patient, the radiation treatment apparatus including:
a radiation emitter positioned to emit a radiation beam, and
a rotating assembly to direct a radiation beam having a beam axis through a target of the patient and having a rotational path in a distinct plane and an axis of rotation, the axis of rotation of the rotating assembly intersecting the beam axis at a three-dimensional coordinate to define an isocenter of an isocenter coordinate system of the treatment apparatus;
a trackable body fixedly connected to a preselected portion of the rotating assembly at a predetermined trackable body offset position relative to a predetermined three-dimensional coordinate position of the isocenter, the trackable body having a plurality of separate and spaced-apart indicators each connected at a separate preselected position thereon and adapted to be tracked to indicate a separate three-dimensional coordinate position of each indicator of the plurality of indicators; and
an apparatus to track a trackable body, the apparatus comprising:
a trackable body detector having a detector body positioned spaced apart from the treatment apparatus and having a receiver positioned to receive energy provided by a subset of the plurality of indicators, to thereby detect three-dimensional positions and to produce a plurality of position signals indicating three-dimensional coordinate positions of the subset of the plurality of indicators, and
a determiner, in communication with the trackable body detector and responsive to the plurality of position signals produced by the detector, to determine the three-dimensional coordinate positions of the subset of the plurality of indicators, to thereby determine the three-dimensional coordinate position of the isocenter of the treatment apparatus and to thereby determine, when so existing, a possible isocenter coordinate system definition failure.

9. A system as defined in claim 8,
wherein the determiner includes a memory associated therewith, a predetermined transform matrix stored in the memory to indicate a transform magnitude, direction, and rotation between a preselected trackable body reference coordinate system and a predetermined isocenter coordinate system; and
wherein the determiner, responsive to the plurality of position signals from the trackable body detector and the predetermined transform matrix, determines the three-dimensional coordinate position of the isocenter.

10. A system as defined in claim 8,
wherein the determiner includes a memory associated therewith, a predetermined transform matrix stored in the memory to indicate a transform magnitude, direction, and rotation between a preselected trackable body reference coordinate system and a predetermined isocenter coordinate system, and geometry analyzing program product stored in the memory to analyze treatment apparatus geometry; and
wherein the geometry analyzing program product includes:
a trackable body position determiner, responsive to the plurality of position signals produced by the trackable body detector, to determine at least one three dimensional coordinate position of the trackable body along the rotational path of the rotating assembly, and
an isocenter position determiner, responsive to the determined at least one three-dimensional coordinate position of the trackable body and the predetermined transform matrix stored in the memory, to determine a respective at least one three-dimensional coordinate position of the isocenter.

11. A system as defined in claim 8, wherein the trackable body is a first trackable body, and wherein the set of the plurality of indicators is a first set of indicators, the system further comprising:

a second trackable body having a proximal body end portion pivotally connected to or adjacent the first trackable body, a free-moving distal body end portion, a medial body portion connected to and extending between the proximal body end portion and the distal body end portion, and having a second set of a plurality of separate and spaced-apart indicators each connected at a separate preselected position of the second trackable body to indicate to the trackable body detector a three-dimensional coordinate position of each indicator in the second set of the plurality of indicators.

12. A system as defined in claim 11, wherein the determiner includes a memory associated therewith, a predetermined transform matrix stored in the memory to indicate a transform magnitude, direction, and rotation between a preselected first trackable body reference coordinate system and a predetermined isocenter coordinate system; and wherein the determiner, responsive to the plurality of position signals from the trackable body detector and the predetermined transform matrix, determines a three-dimensional coordinate position and orientation for each of the first and the second trackable bodies, to thereby determine a respective three-dimensional coordinate position of the isocenter and orientation of the isocenter coordinate system.

13. A system as defined in claim 11, wherein the determiner includes a memory associated therewith, a predetermined transform matrix stored in the memory to indicate a transform magnitude, direction, and rotation between a preselected first trackable body reference coordinate system and a predetermined isocenter coordinate system, and geometry analyzing program product stored in the memory to analyze treatment apparatus geometry; and wherein the geometry analyzing program product includes:

a trackable body orientation determiner, responsive to the plurality of position signals produced by the trackable body detector, to determine a first trackable body orientation of the first trackable body and to determine a second trackable body orientation of the second trackable body, and an isocenter orientation determiner, responsive to the first trackable body orientation, and the second trackable body orientation, to determine an angular difference between the first trackable body orientation and the second trackable body orientation, the angular difference indicating an angle of rotation of the rotating assembly, to thereby determine a three-dimensional orientation of the isocenter coordinate system for the treatment apparatus independent of the angle of rotation of the rotating assembly.

14. A system as defined in claim 11, wherein the first trackable body has a first trackable body orientation;

wherein the first trackable body is substantially fixed to the preselected portion of the rotating assembly of the treatment apparatus so that during rotation of the rotating assembly along the rotational path of the rotating assembly from a preselected angle of rotation of the rotating assembly, the first trackable body orientation rotates by an amount corresponding to an angle of rotation of the preselected portion of the rotating assembly;

wherein the second trackable body has a second trackable body orientation; and wherein the proximal body end portion of the second trackable body is pivotally connected to a non-trackable body mounted to or adjacent the first trackable flat body so that during rotation of the rotating assembly from the preselected angle of rotation, the second trackable body orientation remains substantially constant.

15. A system as defined in claim 9, wherein the predetermined transform matrix is a first predetermined transform matrix, wherein the determined three-dimensional position of the isocenter is a first three-dimensional coordinate position of the isocenter determined with reference to the first trackable body, wherein the trackable body detector is positioned at a location offset from the three-dimensional coordinate position of the isocenter to define a trackable body detector offset position, wherein the determiner has a second predetermined transform matrix stored in the memory to indicate a transform between the predetermined isocenter coordinate system and a trackable body detector reference coordinate system, wherein, responsive to the second predetermined transform matrix, the determiner determines a second three-dimensional coordinate position of the isocenter with reference to the trackable body detector offset position, and wherein the determiner compares the first and the second determined three-dimensional coordinate positions of the isocenter, a substantial difference between the first and the second determined three-dimensional coordinate positions of the isocenter indicating a possible isocenter coordinate system definition failure.

16. A system as defined in claim 10, wherein the predetermined transform matrix is a first predetermined transform matrix;

wherein the determined three-dimensional position of the isocenter is a first three-dimensional coordinate position of the isocenter determined with reference to the three-dimensional coordinate position of the first trackable body;

wherein the trackable body detector has a preselected trackable body detector coordinate system;

wherein the trackable body detector is positioned at a preselected location offset from the three-dimensional coordinate position of the isocenter to define a trackable body detector offset position of the trackable body detector coordinate system;

wherein the determiner has a second predetermined transform matrix stored in the memory to indicate a transform between the predetermined isocenter coordinate system and a preselected trackable body detector coordinate system;

wherein the isocenter position determiner, responsive to the second predetermined transform matrix, determines a second three-dimensional coordinate position of the isocenter with reference to the trackable body detector offset position; and wherein the geometry analyzing program product further includes an isocenter comparator, responsive to the first and the second determined three-dimensional coordinate positions of the isocenter, to compare the first and the second determined three-dimensional coordinate positions of the isocenter, a substantial difference between the first and the second determined three-dimensional coordinate positions of the isocenter indicating a possible isocenter coordinate system definition failure.

17. A system as defined in claim 8, wherein the system further includes a controller, responsive to the treatment plan treatment delivery instructions, to control delivery of the radiation beam to the patient, and wherein the determiner is in communication with the application computer, and wherein the determiner, responsive to determination of a possible isocenter definition failure, when so determined, signals the application computer to at least one of notify an operator a possible definition failure exists, signal the controller to terminate radiation delivery, and signal the controller to adjust radiation beam direction or intensity as necessary to compensate for the possible isocenter definition failure.

18. A system as defined in claim 8,
   wherein the determiner includes a memory associated therewith and a predetermined rotational path of the rotating assembly stored in the memory;
   wherein the determiner, responsive to the plurality of position signals from the trackable body detector, determines a set of first trackable body positions located substantially along the rotational path of the rotating assembly; and
   wherein the determiner compares each first trackable body position of the set of first trackable body positions to the predetermined rotational path to thereby determine if either of the three-dimensional coordinate trackable body positions substantially deviate from a position substantially coincident with the predetermined rotational path, such deviation indicating a possible isocenter definition failure.

19. A system as defined in claim 8,
   wherein the determiner includes a memory associated therewith, and a predetermined rotational path of the rotating assembly stored in the memory, and geometry analyzing program product stored in the memory to analyze treatment apparatus geometry; and
   wherein the geometry analyzing program product includes:
      a trackable body position determiner, responsive to the plurality of position signals produced by the trackable body detector, to determine a plurality of first trackable body positions along the rotational path of the rotating assembly, and
      a rotational path comparator, responsive to the plurality of determined first trackable body positions, to compare the determined plurality of first trackable body positions to the predetermined rotational path to thereby determine if either of the determined plurality of first trackable body positions substantially deviate from a position substantially coincident with the predetermined rotational path of the rotating assembly, such deviation indicating a possible isocenter definition failure.

20. A system as defined in claim 19, wherein the determiner, responsive to determination of a substantial deviation of either of the first trackable body positions from a position substantially coincident with the predetermined rotational path of the rotating assembly, determines a corrected three-dimensional coordinate position of the isocenter.

21. Geometry analyzing program product stored on a storage media to analyze a geometry of a radiation treatment apparatus having a rotating assembly during radiation delivery to thereby detect a possible isocenter coordinate system definition failure so that a treatment plan can be more accurately applied to a patient, the program product comprising:
   a trackable body position and orientation determiner, adapted to receive a plurality of position signals produced by a trackable body detector and indicating a separate three-dimensional coordinate position of a first and a second set of a plurality of trackable indicators connected respectively to a first and a second trackable body, to determine a three-dimensional coordinate first trackable body position and first trackable body orientation of the first trackable body, and to determine a respective second trackable body orientation of the second trackable body;
   an isocenter position and orientation determiner, responsive to the determined first trackable body position, the determined first trackable body orientation, the determined second trackable body orientation, and responsive to a predetermined transform matrix indicating a transform magnitude, direction, and magnitude between a predetermined first trackable body reference coordinate system and a predetermined isocenter coordinate system of the treatment apparatus, to determine a respective three-dimensional coordinate system definition of an isocenter of the isocenter coordinate system and to determine an angular difference between the first trackable body orientation and the second trackable body orientation, the angular difference indicating an angle of rotation of the rotating assembly, to thereby determine an orientation of the isocenter coordinate system for the treatment apparatus independent of the angle of rotation of the rotating assembly;
   a deviation detector, responsive to at least one of the trackable body position and orientation determiner and the isocenter position and orientation determiner, to detect a deviation in the geometry of the rotating assembly, when so existing, such deviation indicating a possible isocenter coordinate system definition failure; and
   a deviation responder, responsive to detection of the deviation, when so existing, to respond to such deviation during application of the treatment plan by signaling an existence of a possible isocenter coordinate system definition failure.

22. Program product as defined in claim 21,
   wherein the predetermined transform matrix is a first predetermined transform matrix;
   wherein the determined three-dimensional coordinate system definition of the isocenter is a first three-dimensional coordinate system definition of the isocenter determined with reference to the first trackable body position;
   wherein the trackable body detector is positioned at a fixed location offset from the three-dimensional coordinate system definition of the isocenter to define a trackable body detector reference offset position;
   wherein the isocenter position and orientation determiner, responsive to a second predetermined transform matrix indicating a transform magnitude, direction, and rotation between a preselected trackable body detector reference coordinate system and the predetermined isocenter coordinate system of the treatment apparatus, determines a second three-dimensional coordinate system definition of the isocenter referenced to the trackable body detector reference offset position; and
   wherein the deviation detector further includes an isocenter comparator, responsive to the first and the second determined three-dimensional coordinate system definitions of the isocenter, to compare the first and the second three-dimensional coordinate system definitions of the isocenter, a substantial difference between the first and the second determined three-dimensional coordinate system definitions of the isocenter indicating a possible isocenter coordinate system definition failure.

23. Program product as defined in claim 21,
wherein the trackable body position and orientation determiner determines a plurality of first trackable body positions located along the rotational path of the rotating assembly; and
wherein the deviation detector further includes a rotational path comparator, responsive to the plurality of determined three-dimensional coordinate first trackable body positions and is positioned to receive a data set defining a predetermined rotational path of the rotating assembly, to determine if either of the plurality of determined three-dimensional coordinate first trackable body positions substantially deviate from a position substantially coincident with the predetermined rotational path of the rotating assembly, such deviation indicating a possible isocenter coordinate system definition failure.

24. Program product as defined in claim 23, wherein the isocenter position and orientation determiner, responsive to the determination of the deviation, determines a corrected three-dimensional coordinate system definition of the isocenter and orientation of the isocenter coordinate system.

25. Program product as defined in claim 24, wherein the corrected three-dimensional coordinate system definition of the isocenter and orientation of the isocenter coordinate system is determined for a plurality of rotational positions along a maximum rotational range of the rotating assembly.

26. Geometry analyzing program product stored on a storage media to analyze a geometry of a treatment apparatus having a rotating assembly to thereby detect a possible isocenter coordinate system definition failure, the program product comprising:
a trackable body position determiner, adapted to receive a plurality of position signals produced by a trackable body detector and indicating a separate position of a plurality of separate and spaced-apart trackable indicators connected to a trackable body fixedly connected to a rotating assembly of a treatment apparatus carrying a radiation emitter and positioned to be rotated along a rotational path of the rotating assembly of the treatment apparatus, to determine a trackable body position of the trackable body; and
an isocenter position determiner, responsive to the determined trackable body position and a predetermined transform matrix indicating a transform magnitude and direction between a predetermined trackable body coordinate system of the trackable body positioned along the rotational path of the rotating assembly of the treatment apparatus and a predetermined isocenter coordinate system of a treatment room, to determine a respective current at least one three-dimensional coordinate position of an isocenter of the isocenter coordinate system of the treatment room during operation of the treatment apparatus to thereby provide isocenter coordinate system definition failure detection when providing patient treatment delivery.

27. Program product as defined in claim 26, further comprising:
a deviation detector, responsive to at least one of the trackable body position determiner and the isocenter position determiner, to detect a deviation in the geometry of the rotating assembly, when so existing, during patient treatment delivery, such deviation indicating a possible isocenter coordinate system definition failure of the isocenter coordinate system of the treatment room; and
a deviation responder, responsive to detection of the deviation, when so existing, to respond to such deviation during application of the treatment plan by signaling an existence of a possible isocenter coordinate system definition failure of the isocenter coordinate system of the treatment room, when so existing.

28. Program product as defined in claim 26,
wherein the trackable body is a first trackable body;
wherein the plurality of position signals produced by the trackable body detector also indicate separate positions of a plurality of separate and spaced-apart trackable indicators connected to a second trackable body also positioned along the rotational path of the rotating assembly; and
wherein the program product further comprises:
a trackable body orientation determiner, responsive to the plurality of position signals produced by the trackable body detector, to determine a first trackable body orientation of the first trackable body and to determine a second trackable body orientation of the second trackable body, and
an isocenter orientation determiner, responsive to the determined first trackable body orientation and the second trackable body orientation, to determine an angular difference between the first trackable body orientation and the second trackable body orientation, the angular difference indicating an angle of rotation of the rotating assembly, to thereby determine an orientation of the isocenter coordinate system independent of the angle of rotation of the rotating assembly.

29. Program product as defined in claim 26,
wherein the predetermined transform matrix is a first predetermined transform matrix;
wherein the determined three-dimensional coordinate position of the isocenter is a first three-dimensional coordinate position of the isocenter determined with reference to the first trackable body position;
wherein the trackable body detector is positioned at a fixed location offset from the three-dimensional coordinate position of the isocenter to define a trackable body detector offset position;
wherein the isocenter position determiner, responsive to a second predetermined transform matrix indicating a transform magnitude and direction between the preselected trackable body detector reference offset position for the trackable body detector and the predetermined three-dimensional coordinate position of the isocenter, determines a second three-dimensional coordinate position of the isocenter with reference to the trackable body detector offset position; and
wherein the program product further includes an isocenter comparator, responsive to the first and the second determined three-dimensional coordinate positions of the isocenter, to compare the first and the second three-dimensional coordinate positions of the isocenter, a substantial difference between the first and the second determined three-dimensional coordinate positions of the isocenter indicating a possible isocenter coordinate system definition failure.

30. Program product as defined in claim 28,
wherein the determined orientation of the isocenter coordinate system is a first orientation of the isocenter coordinate system determined from an angular difference between the first trackable body orientation and the second trackable body orientation;
wherein the isocenter orientation determiner determines a second orientation of the isocenter coordinate system referenced to a trackable body detector reference orientation; and wherein the isocenter comparator, responsive to the first and the second determined orientations of the isocenter coordinate system, compares the first and the second determined orientations of the isocenter coordinate system, a substantial difference between the first and the second determined orientations of the isocenter coordinate system indicating a possible isocenter coordinate system definition failure.

31. Program product as defined in claim 26,
wherein the trackable body position determiner determines a plurality of three-dimensional coordinate trackable body positions located along the rotational path of the rotating assembly; and
wherein the program product further comprises a rotational path comparator, responsive to the plurality of determined trackable body positions and is positioned to receive a predetermined rotational path of the rotating assembly, to determine if either of the plurality of determined trackable body positions substantially deviate from a position substantially coincident with the predetermined rotational path of the rotating assembly, such deviation indicating a possible isocenter coordinate system definition failure.

32. Program product as defined in claim 31, wherein the isocenter position determiner, responsive to the determination of the deviation, determines a corrected three-dimensional coordinate position of the isocenter.

33. Program product as defined in claim 32, wherein the corrected three-dimensional coordinate position of the isocenter is determined for a plurality of rotational positions along a maximum rotational range of the rotating assembly.

34. A computer readable medium that is readable by a computer to monitor a geometry of an apparatus having a rotating assembly, to thereby detect a possible isocenter coordinate system definition failure, the computer readable medium comprising a set of instructions stored thereon that, when executed by the computer, cause the computer to perform the following operations:
   receiving a plurality of position signals produced by a trackable body detector that indicate a separate three-dimensional coordinate position of a plurality of trackable indicators connected respectively to a first trackable body, and that also indicate separate three-dimensional coordinate positions of a plurality of separate and spaced-apart trackable indicators connected to a second trackable body;
   determining a three-dimensional coordinate trackable body position of the first trackable body, responsive to the plurality of position signals;
   receiving a predetermined transform matrix indicating a transform magnitude, direction, and rotation between a predetermined trackable body reference coordinate system and a predetermined isocenter coordinate system of the apparatus;
   responsive to the determined trackable body position and the predetermined transform matrix, determining a respective three-dimensional coordinate system definition of the isocenter of the apparatus;
   determining a first trackable body orientation of the first trackable body and a corresponding second trackable body orientation of the second trackable body, responsive to the plurality of position signals;
   determining an angular difference between the first trackable body orientation and the second trackable body orientation, responsive to the determined first trackable body orientation and the determined second trackable body orientation, the angular difference indicating an angle of rotation of the rotating assembly; and
   responsive to the angle of rotation of the rotating assembly, determining a three-dimensional orientation of the isocenter coordinate system for the apparatus independent of the angle of rotation of the rotating assembly.

35. A computer readable medium that is readable by a computer to monitor a geometry of an apparatus having a rotating assembly to thereby detect a possible isocenter coordinate system definition failure, the computer readable medium comprising a set of instructions stored thereon that, when executed by the computer, cause the computer to perform the following operations:
   receiving a plurality of position signals produced by a trackable body detector that indicate a separate three-dimensional coordinate position of a plurality of trackable indicators connected respectively to a trackable body;
   determining a three-dimensional coordinate trackable body position of the trackable body, responsive to the plurality of position signals;
   receiving a first predetermined transform matrix indicating a transform magnitude, direction, and rotation between a predetermined trackable body reference coordinate system and a predetermined isocenter coordinate system of the apparatus;
   responsive to the determined trackable body position and the predetermined transform matrix, determining a first three-dimensional coordinate system definition of the isocenter of the apparatus with reference to the first trackable body position, the trackable body detector positioned at a fixed location offset from the first three-dimensional coordinate system definition of the isocenter to define a trackable body detector reference offset position;
   receiving a second predetermined transform matrix indicating a transform magnitude, direction, and rotation between a trackable body detector coordinate system for the trackable body detector and the predetermined isocenter coordinate system of the apparatus;
   determining a second three-dimensional coordinate system definition of the isocenter referenced to the trackable body detector offset position, responsive to the second predetermined transform matrix; and
   comparing the first and the second three-dimensional coordinate system definitions of the isocenter, responsive to determine the first and the second determined three-dimensional coordinate system definitions of the isocenter, a substantial difference between the first and the second determined three-dimensional coordinate system definitions of the isocenter indicating a possible isocenter coordinate system definition failure.

36. A computer readable medium that is readable by a computer to monitor during patient treatment delivery a geometry of a treatment apparatus having a rotating assembly to thereby detect a possible isocenter coordinate system definition failure, the computer readable medium comprising a set of instructions stored thereon that, when executed by the computer, cause the computer to perform the following operations:
   receiving a plurality of position signals produced by a trackable body detector that indicate a separate three-dimensional coordinate position of a plurality of separate and spaced-apart trackable indicators connected to a first trackable body positioned along a rotational path of the rotating assembly, and that also indicate separate three-dimensional coordinate positions of a plurality of separate and spaced-apart trackable indicators connected to a second trackable body also positioned along the rotational path of the rotating assembly;

determining during patient treatment delivery a three-dimensional coordinate trackable body position of the first trackable body, responsive to the plurality of position signals;

receiving a predetermined transform matrix indicating a transform between a predetermined trackable body coordinate system of the first trackable body and a predetermined isocenter coordinate system of the treatment apparatus;

determining an at least one three-dimensional coordinate position of the isocenter responsive to the determined three-dimensional coordinate position of the first trackable body and the predetermined transform matrix;

determining a first trackable body orientation of the first trackable body and determining a corresponding second trackable body orientation of the second trackable body, responsive to the plurality of position signals produced by the trackable body detector;

determining an angular difference between the first trackable body orientation and the second trackable body orientation, responsive to the determined first trackable body orientation and the second trackable body orientation, the angular difference indicating an angle of rotation of the rotating assembly; and determining a three-dimensional orientation of the isocenter coordinate system for the treatment apparatus independent of the angle of rotation of the rotating assembly, responsive to the angle of rotation of the rotating assembly.

37. A computer readable medium that is readable by a computer to monitor during patient treatment delivery a geometry of a treatment apparatus having a rotating assembly to thereby detect a possible isocenter coordinate system definition failure, the computer readable medium comprising a set of instructions stored thereon that, when executed by the computer, cause the computer to perform the following operations:

receiving a plurality of position signals produced by a trackable body detector that indicate a separate three-dimensional coordinate position of a plurality of separate and spaced-apart trackable indicators connected to a trackable body positioned along a rotational path of the rotating assembly;

determining during patient treatment delivery a three-dimensional coordinate trackable body position of the trackable body, responsive to the plurality of position signals;

receiving a first predetermined transform matrix indicating a transform between a predetermined trackable body coordinate system of the trackable body and a predetermined isocenter coordinate system of the treatment apparatus;

determining a first three-dimensional coordinate position of the isocenter determined with reference to the first trackable body position responsive to the determined three-dimensional coordinate position of the trackable body and the first predetermined transform matrix, the trackable body detector positioned at a fixed location offset from the first three-dimensional coordinate position of the isocenter to define a trackable body detector offset position;

receiving a second predetermined transform matrix indicating a transform between a trackable body detector coordinate system for the trackable body detector and the predetermined isocenter coordinate system of the treatment apparatus;

determining a second three-dimensional coordinate position of the isocenter with reference to the trackable body detector offset position, responsive to the second predetermined transform matrix; and comparing the first and the second three-dimensional coordinate positions of the isocenter, responsive to the first and the second determined three-dimensional coordinate positions of the isocenter, a substantial difference between the first and the second determined three-dimensional coordinate positions of the isocenter indicating a possible isocenter coordinate system definition failure.

38. A computer readable medium as defined in claim 37, further comprising a set of instructions that, when executed by the computer, cause the computer to perform the following operations:

determining an angle of rotation of the rotating assembly, responsive to the determined first trackable body orientation and the second trackable body orientation; and determining a location of a cause of the possible isocenter coordinate system definition failure, responsive to the determined angle of rotation of the rotating assembly and the possible isocenter definition failure.

39. A computer readable medium as defined in claim 37, wherein the determined orientation of the isocenter coordinate system is a first orientation of the isocenter coordinate system determined from an angular difference between the first trackable body orientation and the second trackable body orientation, the computer readable medium further comprising a set of instructions that, when executed by the computer, cause the computer to perform the following operations:

determining a second orientation of the isocenter coordinate system referenced to a trackable body detector offset position, responsive to the second predetermined transform matrix; and comparing the first and the second determined orientations of the isocenter coordinate system, responsive to the first and the second determined orientations of the isocenter coordinate system, a substantial difference between the first and the second determined orientations of the isocenter coordinate system indicating a possible isocenter coordinate system definition failure.

40. A method of determining an isocenter of a treatment apparatus having a rotating assembly to detect a possible isocenter coordinate system definition failure so that a treatment plan can be more accurately applied to a patient, the method comprising the steps of:

determining a three-dimensional coordinate position of a first trackable body connected to a preselected portion of the rotating assembly and located at a predetermined offset position relative to a predetermined three-dimensional coordinate system definition of an isocenter of an isocenter coordinate system of the treatment apparatus, the first trackable body having a first plurality of separate and spaced apart indicators each connected at a separate preselected position on the trackable body to indicate a separate three-dimensional coordinate position of each indicator of the plurality of indicators, to thereby provide three-dimensional positional data of the trackable body;

determining the three-dimensional coordinate system definition of the isocenter by applying to the determined three-dimensional position of the first trackable body, a predetermined transform matrix indicating a transform between a trackable body reference coordinate system and the isocenter coordinate system;
determining a first trackable body orientation of the first trackable body; and
determining a second trackable body orientation of a second trackable body, the second trackable body having: a proximal body end portion pivotally connected to or adjacent the first trackable body and a free moving distal body end portion to provide a substantially constant reference orientation, a medial body portion connected to and extending between the proximal body end portion and the distal body end portion, and a second plurality of separate and spaced-apart indicators each connected at a separate preselected position on the second trackable body to indicate a separate three-dimensional coordinate position of each indicator of the second plurality of indicators, to thereby provide second trackable body orientation data of the second trackable body.

41. A method as defined in claim 40, further comprising the step of comparing the first trackable body orientation of the first trackable body to the second trackable body orientation of the second trackable body at a sampled point to thereby determine the angular rotation of the rotating assembly at the sampled point.

42. A method as defined in claim 40, wherein the isocenter coordinate system has an orientation relative to the first trackable body orientation, the method further comprising the steps of:
determining an angular difference between the first trackable body orientation of the first trackable body and the second trackable body orientation of the second trackable body, the angular difference indicating an isocenter angular correction factor; and
applying the isocenter angular correction factor to the determined three-dimensional coordinate system definition of the isocenter, to thereby determine an orientation of the isocenter coordinate system for the treatment apparatus independent of angle of rotation of the rotating assembly.

43. A method of monitoring a geometry of a treatment apparatus having a rotating assembly to detect a possible isocenter coordinate system definition failure so that a treatment plan can be more accurately applied to a patient, the method comprising the steps of:
connecting a trackable body to a preselected portion of the rotating assembly located at a predetermined offset position relative to a predetermined three-dimensional coordinate position of an isocenter of the treatment apparatus;
sampling and analyzing at least one position of the trackable body along a rotational path of the rotating assembly to detect a deviation in the geometry of the rotating assembly, when so existing, during application of the treatment plan, to thereby verify a definition of the isocenter coordinate system determined with reference to the trackable body;
detecting a deviation in the geometry of the rotating assembly, when so existing, during application of the treatment plan by:
determining a three-dimensional coordinate position of the trackable body to define a trackable body position,
applying to the trackable body position, a first predetermined transform matrix indicating a transform between a predetermined trackable body reference coordinate system and a predetermined isocenter coordinate system, to thereby determine a first determined isocenter coordinate position,
determining a three-dimensional coordinate position of a portion of an apparatus to track a trackable body to define a trackable body detector offset position,
applying to the trackable body detector offset position, a second predetermined transform matrix indicating a transform between the predetermined trackable body detector offset position and the predetermined three-dimensional coordinate position of the isocenter, to thereby determine a second determined isocenter position, and
comparing the first and the second determined isocenter positions, a substantial difference between the first and the second determined isocenter positions indicating a possible isocenter coordinate system definition failure; and
signaling an existence of a possible isocenter coordinate system definition failure, responsive to detection of the deviation.

44. A method of monitoring a geometry of a treatment apparatus having a rotating assembly to detect a possible isocenter coordinate system definition failure so that a treatment plan can be more accurately applied to a patient, the method comprising the steps of:
connecting a first trackable body to a preselected portion of the rotating assembly located at a predetermined offset position relative to a predetermined three-dimensional coordinate position of an isocenter of the treatment apparatus;
sampling and analyzing at least one position of the trackable body along a rotational path of the rotating assembly to detect a deviation in the geometry of the rotating assembly, when so existing, during application of the treatment plan, to thereby verify a definition of the isocenter coordinate system determined with reference to the trackable body;
detecting a deviation in the geometry of the rotating assembly, when so existing, during application of the treatment plan by:
determining an angular difference between a first trackable body orientation of the first trackable body and a second trackable body orientation of a second trackable body pivotally connected to or adjacent the first trackable body, to thereby determine a first determined orientation of the isocenter,
determining a second determined orientation of the isocenter coordinate system, responsive to a predefined orientation of a portion of the apparatus to track a trackable body, and
comparing the first and the second orientations of the isocenter coordinate system, a substantial difference between the first and the second determined orientations of the isocenter coordinate system indicating a possible isocenter coordinate system definition failure; and
signaling an existence of a possible isocenter coordinate system definition failure, responsive to detection of the deviation.

45. A method of monitoring a geometry of a treatment apparatus having a rotating assembly to detect a possible isocenter coordinate system definition failure so that a treatment plan can be more accurately applied to a patient, the method comprising the steps of:
connecting a trackable body to a preselected portion of the rotating assembly located at a predetermined offset position relative to a predetermined three-dimensional coordinate position of an isocenter of the treatment apparatus;

sampling and analyzing at least one position of the trackable body along a rotational path of the rotating assembly to detect a deviation in the geometry of the rotating assembly, when so existing, during application of the treatment plan, to thereby verify a definition of the isocenter coordinate system determined with reference to the trackable body;

detecting a deviation in the geometry of the rotating assembly, when so existing, during application of the treatment plan by:

determining a plurality of three-dimensional coordinate trackable body positions for the trackable body located along the rotational path of the rotating assembly, and comparing each of the determined three-dimensional coordinate trackable body positions to a predetermined rotational path of the rotating assembly, to determine if either of the plurality of determined three-dimensional coordinate trackable body positions substantially deviate from a position substantially coincident with the predetermined rotational path of the rotating assembly, such deviation indicating a possible isocenter coordinate system definition failure; and signaling an existence of a possible isocenter coordinate system definition failure, responsive to detection of the deviation.

46. A method as defined in claim 45, wherein the step of responding to detection of the deviation further comprises the step of determining a corrected three-dimensional coordinate position of the isocenter.

47. A method as defined in claim 46, wherein the corrected three-dimensional coordinate position of the isocenter is determined for a plurality of rotational positions along a maximum rotational range of the rotating assembly.

* * * * *